US011229517B2

(12) United States Patent
Adamek-Bowers et al.

(10) Patent No.: US 11,229,517 B2
(45) Date of Patent: Jan. 25, 2022

(54) REPLACEMENT HEART VALVE COMMISSURE ASSEMBLY

(71) Applicant: BOSTON SCIENTIFIC SCIMED, INC., Maple Grove, MN (US)

(72) Inventors: Jasper Ellington Adamek-Bowers, San Francisco, CA (US); Ali Salahieh, Saratoga, CA (US); Anh Thu Pham, San Jose, CA (US); Dwight John Knab, Jr., Newark, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 170 days.

(21) Appl. No.: 16/413,056

(22) Filed: May 15, 2019

(65) Prior Publication Data

US 2019/0350701 A1 Nov. 21, 2019

Related U.S. Application Data

(60) Provisional application No. 62/671,520, filed on May 15, 2018.

(51) Int. Cl.
*A61F 2/24* (2006.01)
(52) U.S. Cl.
CPC ............ *A61F 2/243* (2013.01); *A61F 2/2463* (2013.01); *A61F 2/2412* (2013.01)
(58) Field of Classification Search
CPC .......... A61F 2/24; A61F 2/243; A61F 2/2463; A61F 2/2412; A61F 2/2409; A61F 2/2418
See application file for complete search history.

(56) References Cited

U.S. PATENT DOCUMENTS

| 15,192 A | 6/1856 | Peale |
| 2,682,057 A | 6/1954 | Lord |

(Continued)

FOREIGN PATENT DOCUMENTS

| AU | 2002329324 B2 | 7/2007 |
| CN | 1338951 A | 3/2002 |

(Continued)

OTHER PUBLICATIONS

US 8,062,356 B2, 11/2011, Salahieh et al. (withdrawn)

(Continued)

*Primary Examiner* — Yashita Sharma
*Assistant Examiner* — Amanda M Barkan
(74) *Attorney, Agent, or Firm* — Seager, Tufte & Wickhem LLP

(57) ABSTRACT

A replacement heart valve commissure assembly may include: a locking mechanism including a first locking portion spaced apart from a second locking portion in a delivery configuration and configured to engage the second locking portion in a deployed configuration, the first locking portion being longitudinally actuatable relative to the second locking portion between the delivery and deployed configurations; and first and second valve leaflets secured to the first locking portion. A first sleeve portion of the first valve leaflet may be fixedly attached to a first fabric sleeve wrapped around a first leg of the first locking portion. A second sleeve portion of the second valve leaflet may be fixedly attached to a second fabric sleeve wrapped around a second leg of the first locking portion. The first fabric sleeve may include first and second end portions, and an elastic central portion configured to engage the first leg.

13 Claims, 18 Drawing Sheets

(56) References Cited

U.S. PATENT DOCUMENTS

| | | |
|---|---|---|
| 2,701,559 A | 2/1955 | Cooper |
| 2,832,078 A | 4/1958 | Williams |
| 3,029,819 A | 4/1962 | Starks |
| 3,099,016 A | 7/1963 | Lowell |
| 3,113,586 A | 12/1963 | Edmark |
| 3,130,418 A | 4/1964 | Head et al. |
| 3,143,742 A | 8/1964 | Cromie |
| 3,221,006 A | 11/1965 | Moore et al. |
| 3,334,629 A | 8/1967 | Cohn |
| 3,365,728 A | 1/1968 | Edwards et al. |
| 3,367,364 A | 2/1968 | Cruz et al. |
| 3,409,013 A | 11/1968 | Henry |
| 3,445,916 A | 5/1969 | Schulte |
| 3,540,431 A | 11/1970 | Mobin-Uddin |
| 3,548,417 A | 12/1970 | Kischer et al. |
| 3,570,014 A | 3/1971 | Hancock |
| 3,587,115 A | 6/1971 | Shiley |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Goodenough et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,084,268 A | 4/1978 | Ionescu et al. |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Tassel et al. |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten et al. |
| 4,662,885 A | 5/1987 | DiPisa |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz et al. |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thuroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,122,154 A | 6/1992 | Rhodes |
| 5,132,473 A | 7/1992 | Furutaka et al. |
| 5,141,494 A | 8/1992 | Danforth et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,238,004 A | 8/1993 | Sahatjian et al. |
| 5,258,023 A | 11/1993 | Reger |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,739 A | 6/1995 | Jessen |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,469,868 A | 11/1995 | Reger |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,489,297 A | 2/1996 | Duran |
| 5,500,014 A | 3/1996 | Quijano et al. |

(56) References Cited

U.S. PATENT DOCUMENTS

| | | |
|---|---|---|
| 5,507,767 A | 4/1996 | Maeda et al. |
| 5,522,881 A | 6/1996 | Lentz |
| 5,534,007 A | 7/1996 | Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,784 A | 5/1997 | Strecker |
| 5,645,559 A | 7/1997 | Hacllman et al. |
| 5,653,745 A | 8/1997 | Trescony et al. |
| 5,662,671 A | 9/1997 | Barbut et al. |
| 5,667,523 A | 9/1997 | Bynon et al. |
| 5,674,277 A | 10/1997 | Freitag |
| 5,681,345 A | 10/1997 | Euteneuer |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,709,713 A | 1/1998 | Evans et al. |
| 5,713,951 A | 2/1998 | Garrison et al. |
| 5,713,953 A | 2/1998 | Vallana et al. |
| 5,716,370 A | 2/1998 | Williamson et al. |
| 5,716,417 A | 2/1998 | Girard et al. |
| 5,720,391 A | 2/1998 | Dohm et al. |
| 5,725,549 A | 3/1998 | Lam |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,755,783 A | 5/1998 | Stobie et al. |
| 5,756,476 A | 5/1998 | Epstein et al. |
| 5,769,812 A | 6/1998 | Stevens et al. |
| 5,769,882 A | 6/1998 | Fogarty et al. |
| 5,772,609 A | 6/1998 | Nguyen et al. |
| 5,776,188 A | 7/1998 | Shepherd et al. |
| 5,782,904 A | 7/1998 | White et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,037 A | 10/1998 | Fogarty et al. |
| 5,824,041 A | 10/1998 | Lenker et al. |
| 5,824,043 A | 10/1998 | Cottone |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,843,161 A | 12/1998 | Solovay |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,419 A | 3/1999 | Carpenter et al. |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,015,431 A | 1/2000 | Thornton et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson et al. |
| 6,051,014 A | 4/2000 | Jang |
| 6,059,827 A | 5/2000 | Fenton |
| 6,074,418 A | 6/2000 | Buchanan et al. |
| 6,093,203 A | 7/2000 | Uflacker |
| 6,096,074 A | 8/2000 | Pedros |
| 6,110,198 A | 8/2000 | Fogarty et al. |
| 6,123,723 A | 9/2000 | Konya et al. |
| 6,132,473 A | 10/2000 | Williams et al. |
| 6,139,510 A | 10/2000 | Palermo |
| 6,142,987 A | 11/2000 | Tsugita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,911 B1 | 3/2001 | Milo |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,258,129 B1 | 7/2001 | Dybdal et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,306,164 B1 | 10/2001 | Kujawski |
| 6,309,417 B1 | 10/2001 | Spence et al. |
| 6,312,465 B1 | 11/2001 | Griffin et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,554 B2 | 3/2002 | Paulis |
| 6,352,708 B1 | 3/2002 | Duran et al. |
| 6,361,545 B1 | 3/2002 | Macoviak et al. |
| 6,363,938 B2 | 4/2002 | Saadat et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |

(56) References Cited

U.S. PATENT DOCUMENTS

| | | |
|---|---|---|
| 6,387,122 B1 | 5/2002 | Cragg |
| 6,398,807 B1 | 6/2002 | Chouinard et al. |
| 6,402,736 B1 | 6/2002 | Brown et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,803 B1 | 1/2003 | Horikawa et al. |
| 6,508,833 B2 | 1/2003 | Pavcnik et al. |
| 6,527,800 B1 | 3/2003 | McGuckin et al. |
| 6,530,949 B2 | 3/2003 | Konya et al. |
| 6,530,952 B2 | 3/2003 | Vesely |
| 6,537,297 B2 | 3/2003 | Tsugita et al. |
| 6,540,768 B1 | 4/2003 | Diaz et al. |
| 6,540,782 B1 | 4/2003 | Snyders |
| 6,562,058 B2 | 5/2003 | Seguin et al. |
| 6,569,196 B1 | 5/2003 | Vesely |
| 6,572,643 B1 | 6/2003 | Gharibadeh |
| 6,585,766 B1 | 7/2003 | Huynh et al. |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,842 B1 | 3/2004 | Gifford et al. |
| 6,712,843 B2 | 3/2004 | Elliott |
| 6,714,842 B1 | 3/2004 | Ito |
| 6,719,789 B2 | 4/2004 | Cox |
| 6,723,116 B2 | 4/2004 | Taheri |
| 6,729,356 B1 | 5/2004 | Baker et al. |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,755,854 B2 | 6/2004 | Gillick et al. |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | Germain et al. |
| 6,769,434 B2 | 8/2004 | Liddicoat et al. |
| 6,773,454 B2 | 8/2004 | Wholey et al. |
| 6,773,456 B1 | 8/2004 | Gordon et al. |
| 6,776,791 B1 | 8/2004 | Stallings et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,002 B2 | 9/2004 | Spence et al. |
| 6,814,746 B2 | 11/2004 | Thompson et al. |
| 6,814,754 B2 | 11/2004 | Greenhalgh |
| 6,821,297 B2 | 11/2004 | Snyders |
| 6,824,041 B2 | 11/2004 | Grieder et al. |
| 6,830,585 B1 | 12/2004 | Artof et al. |
| 6,837,901 B2 | 1/2005 | Rabkin et al. |
| 6,840,957 B2 | 1/2005 | DiMatteo et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,936,058 B2 | 8/2005 | Forde et al. |
| 6,936,067 B2 | 8/2005 | Buchanan |
| 6,939,352 B2 | 9/2005 | Buzzard et al. |
| 6,951,571 B1 | 10/2005 | Srivastava |
| 6,953,332 B1 | 10/2005 | Kurk et al. |
| 6,964,673 B2 | 11/2005 | Tsugita et al. |
| 6,969,395 B2 | 11/2005 | Eskuri |
| 6,972,025 B2 | 12/2005 | WasDyke |
| 6,974,464 B2 | 12/2005 | Quijano et al. |
| 6,974,474 B2 | 12/2005 | Pavcnik et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 6,989,027 B2 | 1/2006 | Allen et al. |
| 7,004,176 B2 | 2/2006 | Lau |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,041,132 B2 | 5/2006 | Quijano et al. |
| 7,044,966 B2 | 5/2006 | Svanidze et al. |
| 7,097,658 B2 | 8/2006 | Oktay |
| 7,108,715 B2 | 9/2006 | Lawrence-Brown et al. |
| 7,122,020 B2 | 10/2006 | Mogul |
| 7,125,418 B2 | 10/2006 | Duran et al. |
| 7,141,063 B2 | 11/2006 | White et al. |
| 7,147,663 B1 | 12/2006 | Berg et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,189,258 B2 | 3/2007 | Johnson et al. |
| 7,191,018 B2 | 3/2007 | Gielen et al. |
| 7,201,772 B2 | 4/2007 | Schwammenthal et al. |
| 7,235,093 B2 | 6/2007 | Gregorich |

(56) References Cited

U.S. PATENT DOCUMENTS

| | | |
|---|---|---|
| 7,252,682 B2 | 8/2007 | Seguin |
| 7,258,696 B2 | 8/2007 | Rabkin et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,322,932 B2 | 1/2008 | Xie et al. |
| 7,326,236 B2 | 2/2008 | Andreas et al. |
| 7,329,279 B2 | 2/2008 | Haug et al. |
| 7,331,993 B2 | 2/2008 | White |
| 7,374,560 B2 | 5/2008 | Ressemann et al. |
| 7,381,219 B2 | 6/2008 | Salahieh et al. |
| 7,381,220 B2 | 6/2008 | Macoviak et al. |
| 7,399,315 B2 | 7/2008 | Iobbi |
| 7,445,631 B2 | 11/2008 | Salahieh et al. |
| 7,470,285 B2 | 12/2008 | Nugent et al. |
| 7,491,232 B2 | 2/2009 | Bolduc et al. |
| 7,510,574 B2 | 3/2009 | Lêet al. |
| 7,524,330 B2 | 4/2009 | Berreklouw |
| 7,530,995 B2 | 5/2009 | Quijano et al. |
| 7,544,206 B2 | 6/2009 | Cohn |
| 7,622,276 B2 | 11/2009 | Cunanan et al. |
| 7,628,803 B2 | 12/2009 | Pavcnik et al. |
| 7,632,298 B2 | 12/2009 | Hijlkema et al. |
| 7,641,687 B2 | 1/2010 | Chinn et al. |
| 7,674,282 B2 | 3/2010 | Wu et al. |
| 7,712,606 B2 | 5/2010 | Salahieh et al. |
| 7,722,638 B2 | 5/2010 | Deyette et al. |
| 7,722,662 B2 | 5/2010 | Steinke et al. |
| 7,722,666 B2 | 5/2010 | Lafontaine |
| 7,731,742 B2 | 6/2010 | Schlick et al. |
| 7,736,388 B2 | 6/2010 | Goldfarb et al. |
| 7,748,389 B2 | 7/2010 | Salahieh et al. |
| 7,758,625 B2 | 7/2010 | Wu et al. |
| 7,780,725 B2 | 8/2010 | Haug et al. |
| 7,799,065 B2 | 9/2010 | Pappas |
| 7,803,185 B2 | 9/2010 | Gabbay |
| 7,824,442 B2 | 11/2010 | Salahieh et al. |
| 7,824,443 B2 | 11/2010 | Salahieh et al. |
| 7,833,262 B2 | 11/2010 | McGuckin et al. |
| 7,846,204 B2 | 12/2010 | Letac et al. |
| 7,857,845 B2 | 12/2010 | Stacchino et al. |
| 7,892,292 B2 | 2/2011 | Stack et al. |
| 7,918,880 B2 | 4/2011 | Austin |
| 7,938,851 B2 | 5/2011 | Olson et al. |
| 7,959,666 B2 | 6/2011 | Salahieh et al. |
| 7,959,672 B2 | 6/2011 | Salahieh et al. |
| 7,988,724 B2 | 8/2011 | Salahieh et al. |
| 8,048,153 B2 | 11/2011 | Salahieh et al. |
| 8,052,749 B2 | 11/2011 | Salahieh et al. |
| 8,136,659 B2 | 3/2012 | Salahieh et al. |
| 8,157,853 B2 | 4/2012 | Laske et al. |
| 8,172,896 B2 | 5/2012 | McNamara et al. |
| 8,182,528 B2 | 5/2012 | Salahieh et al. |
| 8,192,351 B2 | 6/2012 | Fishier et al. |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,213 B2 | 1/2013 | Salahieh et al. |
| 8,376,865 B2 | 2/2013 | Forster et al. |
| 8,377,117 B2 | 2/2013 | Keidar et al. |
| 8,398,708 B2 | 3/2013 | Meiri et al. |
| 8,403,983 B2 | 3/2013 | Quadri et al. |
| 8,414,644 B2 | 4/2013 | Quadri et al. |
| 8,579,962 B2 | 11/2013 | Salahieh et al. |
| 8,603,160 B2 | 12/2013 | Salahieh et al. |
| 8,617,236 B2 | 12/2013 | Paul et al. |
| 8,623,074 B2 | 1/2014 | Ryan |
| 8,623,076 B2 | 1/2014 | Salahieh et al. |
| 8,623,078 B2 | 1/2014 | Salahieh et al. |
| 8,668,733 B2 | 3/2014 | Haug et al. |
| 8,673,000 B2 | 3/2014 | Tabor et al. |
| 8,696,743 B2 | 4/2014 | Holecek et al. |
| 8,828,078 B2 | 9/2014 | Salahieh et al. |
| 8,840,662 B2 | 9/2014 | Salahieh et al. |
| 8,840,663 B2 | 9/2014 | Salahieh et al. |
| 8,858,620 B2 | 10/2014 | Salahieh et al. |
| 8,894,703 B2 | 11/2014 | Salahieh et al. |
| 8,951,299 B2 | 2/2015 | Paul et al. |
| 8,992,608 B2 | 3/2015 | Haug et al. |
| 9,005,273 B2 | 4/2015 | Salahieh et al. |
| 9,011,521 B2 | 4/2015 | Haug et al. |
| 9,168,131 B2 | 10/2015 | Yohanan et al. |
| 9,393,110 B2 * | 7/2016 | Levi ................. A61F 2/2412 |
| 9,510,942 B2 * | 12/2016 | Benichou ........... A61F 2/2415 |
| 9,757,230 B2 * | 9/2017 | Fahim ............... A61F 2/2418 |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0021872 A1 | 9/2001 | Bailey et al. |
| 2001/0025196 A1 | 9/2001 | Chinn et al. |
| 2001/0027338 A1 | 10/2001 | Greenberg |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044634 A1 | 11/2001 | Michael et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029014 A1 | 3/2002 | Jayaraman |
| 2002/0029981 A1 | 3/2002 | Nigam |
| 2002/0032480 A1 | 3/2002 | Spence et al. |
| 2002/0032481 A1 | 3/2002 | Gabbay |
| 2002/0042651 A1 | 4/2002 | Liddicoat et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055774 A1 | 5/2002 | Liddicoat |
| 2002/0058987 A1 | 5/2002 | Butaric et al. |
| 2002/0058995 A1 | 5/2002 | Stevens |
| 2002/0077696 A1 | 6/2002 | Zadno-Azizi et al. |
| 2002/0082609 A1 | 6/2002 | Green |
| 2002/0095173 A1 | 7/2002 | Mazzocchi et al. |
| 2002/0095209 A1 | 7/2002 | Zadno-Azizi et al. |
| 2002/0111674 A1 | 8/2002 | Chouinard et al. |
| 2002/0120328 A1 | 8/2002 | Pathak et al. |
| 2002/0123802 A1 | 9/2002 | Snyders |
| 2002/0138138 A1 | 9/2002 | Yang |
| 2002/0144696 A1 * | 10/2002 | Sharkawy ........... A61F 2/2493 128/898 |
| 2002/0151970 A1 | 10/2002 | Garrison et al. |
| 2002/0156522 A1 | 10/2002 | Ivancev et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0165576 A1 | 11/2002 | Boyle et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0057156 A1 | 3/2003 | Peterson et al. |

(56) References Cited

U.S. PATENT DOCUMENTS

| | | |
|---|---|---|
| 2003/0060844 A1 | 3/2003 | Borillo et al. |
| 2003/0069492 A1 | 4/2003 | Abrams et al. |
| 2003/0069646 A1 | 4/2003 | Stinson |
| 2003/0070944 A1 | 4/2003 | Nigam |
| 2003/0074058 A1 | 4/2003 | Sherry |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0125795 A1 | 7/2003 | Pavcnik et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0165352 A1 | 9/2003 | Ibrahim et al. |
| 2003/0171803 A1 | 9/2003 | Shimon |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0191516 A1 | 10/2003 | Weldon et al. |
| 2003/0195609 A1 | 10/2003 | Berenstein et al. |
| 2003/0199759 A1 | 10/2003 | Richard |
| 2003/0199913 A1 | 10/2003 | Dubrul et al. |
| 2003/0199971 A1 | 10/2003 | Tower et al. |
| 2003/0199972 A1 | 10/2003 | Zadno-Azizi et al. |
| 2003/0204249 A1 | 10/2003 | Letort |
| 2003/0208224 A1 | 11/2003 | Broome |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216774 A1 | 11/2003 | Larson |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2003/0236567 A1 | 12/2003 | Elliot |
| 2004/0019374 A1 | 1/2004 | Hojeibane et al. |
| 2004/0033364 A1 | 2/2004 | Spiridigliozzi et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0059409 A1 | 3/2004 | Stenzel |
| 2004/0073198 A1 | 4/2004 | Gilson et al. |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskur |
| 2004/0088045 A1 | 5/2004 | Cox |
| 2004/0093016 A1 | 5/2004 | Root et al. |
| 2004/0093060 A1 | 5/2004 | Seguin et al. |
| 2004/0097788 A1 | 5/2004 | Mourlas et al. |
| 2004/0098022 A1 | 5/2004 | Barone |
| 2004/0098098 A1 | 5/2004 | McGuckin et al. |
| 2004/0098099 A1 | 5/2004 | McCullagh et al. |
| 2004/0098112 A1 | 5/2004 | DiMatteo et al. |
| 2004/0107004 A1 | 6/2004 | Levine et al. |
| 2004/0111096 A1 | 6/2004 | Tu et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0122468 A1 | 6/2004 | Yodfat et al. |
| 2004/0122516 A1 | 6/2004 | Fogarty et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0167620 A1 | 8/2004 | Ortiz et al. |
| 2004/0181140 A1 | 9/2004 | Falwell et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204755 A1 | 10/2004 | Robin |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225353 A1 | 11/2004 | McGuckin et al. |
| 2004/0225354 A1 | 11/2004 | Allen et al. |
| 2004/0225355 A1 | 11/2004 | Stevens |
| 2004/0243221 A1 | 12/2004 | Fawzi et al. |
| 2004/0254636 A1 | 12/2004 | Flagle et al. |
| 2004/0260390 A1 | 12/2004 | Sarac et al. |
| 2005/0010287 A1 | 1/2005 | Macoviak et al. |
| 2005/0021136 A1 | 1/2005 | Xie et al. |
| 2005/0033398 A1 | 2/2005 | Seguin |
| 2005/0033402 A1 | 2/2005 | Cully et al. |
| 2005/0043711 A1 | 2/2005 | Corcoran et al. |
| 2005/0043757 A1 | 2/2005 | Arad et al. |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060029 A1 | 3/2005 | Le et al. |
| 2005/0065594 A1 | 3/2005 | DiMatteo et al. |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075724 A1 | 4/2005 | Svanidze et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0090890 A1 | 4/2005 | Wu et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0131438 A1 | 6/2005 | Cohn |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |

(56) References Cited

U.S. PATENT DOCUMENTS

| | | |
|---|---|---|
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143807 A1 | 6/2005 | Pavcnik et al. |
| 2005/0143809 A1 | 6/2005 | Salahieh et al. |
| 2005/0149159 A1 | 7/2005 | Andreas et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1 | 12/2005 | Boudjemline |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0025857 A1 | 2/2006 | Bergheim et al. |
| 2006/0058872 A1 | 3/2006 | Salahieh et al. |
| 2006/0149360 A1 | 7/2006 | Schwammenthal et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2006/0287717 A1 | 12/2006 | Rowe et al. |
| 2007/0010876 A1 | 1/2007 | Salahieh et al. |
| 2007/0010877 A1 | 1/2007 | Salahieh et al. |
| 2007/0016286 A1 | 1/2007 | Herrmann et al. |
| 2007/0055340 A1 | 3/2007 | Pryor |
| 2007/0061008 A1 | 3/2007 | Salahieh et al. |
| 2007/0112355 A1 | 5/2007 | Salahieh et al. |
| 2007/0118214 A1 | 5/2007 | Salahieh et al. |
| 2007/0162107 A1 | 7/2007 | Haug et al. |
| 2007/0173918 A1 | 7/2007 | Dreher et al. |
| 2007/0203503 A1 | 8/2007 | Salahieh et al. |
| 2007/0244552 A1 | 10/2007 | Salahieh et al. |
| 2007/0288089 A1 | 12/2007 | Gurskis et al. |
| 2008/0009940 A1 | 1/2008 | Cribier |
| 2008/0033541 A1 | 2/2008 | Gelbart et al. |
| 2008/0071363 A1 | 3/2008 | Tuval et al. |
| 2008/0082165 A1 | 4/2008 | Wilson et al. |
| 2008/0125859 A1 | 5/2008 | Salahieh et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0255661 A1 | 10/2008 | Straubinger et al. |
| 2008/0269878 A1 | 10/2008 | Iobbi |
| 2008/0288054 A1 | 11/2008 | Pulnev et al. |
| 2009/0005863 A1 | 1/2009 | Goeiz et al. |
| 2009/0030512 A1 | 1/2009 | Thielen et al. |
| 2009/0054969 A1 | 2/2009 | Salahieh et al. |
| 2009/0076598 A1 | 3/2009 | Salahieh et al. |
| 2009/0093877 A1 | 4/2009 | Keidar et al. |
| 2009/0157175 A1 | 6/2009 | Benichou |
| 2009/0171456 A1 | 7/2009 | Kveen et al. |
| 2009/0216312 A1 | 8/2009 | Straubinger et al. |
| 2009/0222076 A1 | 9/2009 | Figulla et al. |
| 2009/0264759 A1 | 10/2009 | Byrd |
| 2009/0264997 A1 | 10/2009 | Salahieh et al. |
| 2009/0292350 A1 | 11/2009 | Eberhardt et al. |
| 2009/0299462 A1 | 12/2009 | Fawzi et al. |
| 2010/0036479 A1 | 2/2010 | Hill et al. |
| 2010/0049313 A1 | 2/2010 | Mon et al. |
| 2010/0082089 A1 | 4/2010 | Quadri et al. |
| 2010/0094399 A1 | 4/2010 | Dorn et al. |
| 2010/0121434 A1 | 5/2010 | Paul et al. |
| 2010/0161045 A1 | 6/2010 | Righini |
| 2010/0185275 A1 | 7/2010 | Richter et al. |
| 2010/0191320 A1 | 7/2010 | Straubinger et al. |
| 2010/0191326 A1 | 7/2010 | Alkhatib |
| 2010/0219092 A1 | 9/2010 | Salahieh et al. |
| 2010/0249908 A1 | 9/2010 | Chau et al. |
| 2010/0280495 A1 | 11/2010 | Paul et al. |
| 2010/0298931 A1 | 11/2010 | Quadri et al. |
| 2011/0257735 A1 | 10/2011 | Salahieh et al. |
| 2011/0264196 A1 | 10/2011 | Savage et al. |
| 2011/0276129 A1 | 11/2011 | Salahieh et al. |
| 2011/0288634 A1 | 11/2011 | Tuval et al. |
| 2011/0295363 A1 | 12/2011 | Girard et al. |
| 2012/0016469 A1 | 1/2012 | Salahieh et al. |
| 2012/0016471 A1 | 1/2012 | Salahieh et al. |
| 2012/0022642 A1 | 1/2012 | Haug et al. |
| 2012/0029627 A1 | 2/2012 | Salahieh et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0089224 A1 | 4/2012 | Haug et al. |
| 2012/0132547 A1 | 5/2012 | Salahieh et al. |
| 2012/0179244 A1 | 7/2012 | Schankereli et al. |
| 2012/0197379 A1 | 8/2012 | Laske et al. |
| 2012/0303113 A1 | 11/2012 | Benichou et al. |
| 2012/0303116 A1 | 11/2012 | Gorman et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030520 A1 | 1/2013 | Lee et al. |
| 2013/0079867 A1 | 3/2013 | Hoffman et al. |
| 2013/0079869 A1 | 3/2013 | Straubinger et al. |
| 2013/0096664 A1 | 4/2013 | Goetz et al. |
| 2013/0123796 A1 | 5/2013 | Sutton et al. |
| 2013/0138207 A1 | 5/2013 | Quadri et al. |
| 2013/0158656 A1 | 6/2013 | Sutton et al. |
| 2013/0184813 A1 | 7/2013 | Quadri et al. |
| 2013/0190865 A1 | 7/2013 | Anderson |
| 2013/0304199 A1 | 11/2013 | Sutton et al. |
| 2014/0018911 A1 | 1/2014 | Zhou et al. |
| 2014/0094904 A1 | 4/2014 | Salahieh et al. |
| 2014/0114405 A1 | 4/2014 | Paul et al. |
| 2014/0114406 A1 | 4/2014 | Salahieh et al. |
| 2014/0121766 A1 | 5/2014 | Salahieh et al. |
| 2014/0135912 A1 | 5/2014 | Salahieh et al. |
| 2014/0243967 A1 | 8/2014 | Salahieh et al. |
| 2014/0277418 A1 | 9/2014 | Miller |
| 2014/0364943 A1 | 12/2014 | Conklin |
| 2015/0012085 A1 | 1/2015 | Salahieh et al. |
| 2015/0073540 A1 | 3/2015 | Salahieh et al. |
| 2015/0073541 A1 | 3/2015 | Salahieh et al. |
| 2015/0127094 A1 | 5/2015 | Salahieh et al. |
| 2015/0265401 A1 | 9/2015 | Braido et al. |
| 2016/0045307 A1 | 2/2016 | Yohanan et al. |
| 2016/0067040 A1 | 3/2016 | Agrawal et al. |
| 2016/0143731 A1 | 5/2016 | Backus |
| 2016/0199184 A1 | 7/2016 | Ma et al. |
| 2016/0220359 A1 | 8/2016 | Backus et al. |
| 2016/0220365 A1 | 8/2016 | Backus et al. |
| 2016/0354203 A1 | 12/2016 | Tuval et al. |

(56) References Cited

U.S. PATENT DOCUMENTS

| | | |
|---|---|---|
| 2016/0374802 A1 | 12/2016 | Levi et al. |
| 2017/0056167 A1 | 3/2017 | Tuval |

FOREIGN PATENT DOCUMENTS

| | | |
|---|---|---|
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049814 A1 | 4/2002 |
| DE | 10049815 A1 | 4/2002 |
| EP | 0103546 B1 | 5/1988 |
| EP | 0144167 B1 | 11/1989 |
| EP | 579523 A1 | 1/1994 |
| EP | 0409929 B1 | 4/1997 |
| EP | 0850607 A1 | 7/1998 |
| EP | 0597967 B1 | 12/1999 |
| EP | 1000590 A1 | 5/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 0937439 B1 | 9/2003 |
| EP | 1340473 A2 | 9/2003 |
| EP | 1356793 A3 | 3/2004 |
| EP | 1042045 B1 | 5/2004 |
| EP | 0819013 B1 | 6/2004 |
| EP | 1430853 A2 | 6/2004 |
| EP | 1435879 A1 | 7/2004 |
| EP | 1439800 A2 | 7/2004 |
| EP | 1469797 A1 | 10/2004 |
| EP | 1472996 A1 | 11/2004 |
| EP | 1229864 B1 | 4/2005 |
| EP | 1059894 B1 | 7/2005 |
| EP | 1551274 A2 | 7/2005 |
| EP | 1551336 A1 | 7/2005 |
| EP | 1562515 A1 | 8/2005 |
| EP | 1570809 A1 | 9/2005 |
| EP | 1576937 A2 | 9/2005 |
| EP | 1582178 A2 | 10/2005 |
| EP | 1582179 A2 | 10/2005 |
| EP | 1589902 A1 | 11/2005 |
| EP | 1600121 A1 | 11/2005 |
| EP | 1156757 B1 | 12/2005 |
| EP | 1616531 A2 | 1/2006 |
| EP | 1605871 B1 | 7/2008 |
| EP | 2749254 B1 | 6/2015 |
| EP | 2926766 A1 | 10/2015 |
| FR | 2788217 A1 | 7/2000 |
| GB | 2056023 A | 3/1981 |
| GB | 2398245 A | 8/2004 |
| SU | 1271508 A1 | 11/1986 |
| SU | 1371700 A1 | 2/1988 |
| WO | 9117720 A1 | 11/1991 |
| WO | 9217118 A1 | 10/1992 |
| WO | 9301768 A1 | 2/1993 |
| WO | 9315693 A1 | 8/1993 |
| WO | 9504556 A2 | 2/1995 |
| WO | 9529640 A1 | 11/1995 |
| WO | 9614032 A1 | 5/1996 |
| WO | 9624306 A1 | 8/1996 |
| WO | 9640012 A1 | 12/1996 |
| WO | 9748350 A1 | 12/1997 |
| WO | 9829057 A1 | 7/1998 |
| WO | 9836790 A1 | 8/1998 |
| WO | 9850103 A1 | 11/1998 |
| WO | 9855047 A1 | 12/1998 |
| WO | 9857599 A2 | 12/1998 |
| WO | 9933414 A1 | 7/1999 |
| WO | 9940964 A1 | 8/1999 |
| WO | 9944542 A2 | 9/1999 |
| WO | 9947075 A1 | 9/1999 |
| WO | 9951165 A1 | 10/1999 |
| WO | 0009059 A2 | 2/2000 |
| WO | 2000009059 A2 | 2/2000 |
| WO | 0041652 A1 | 7/2000 |
| WO | 0044308 A2 | 8/2000 |
| WO | 0044311 A2 | 8/2000 |
| WO | 0044313 A1 | 8/2000 |
| WO | 0045874 A1 | 8/2000 |
| WO | 0047139 A1 | 8/2000 |
| WO | 0049970 A1 | 8/2000 |
| WO | 0067661 A2 | 11/2000 |
| WO | 0105331 A1 | 1/2001 |
| WO | 0106959 A1 | 2/2001 |
| WO | 0108596 A1 | 2/2001 |
| WO | 0110320 A1 | 2/2001 |
| WO | 0110343 A1 | 2/2001 |
| WO | 0135870 A1 | 5/2001 |
| WO | 0149213 A2 | 7/2001 |
| WO | 0154625 A1 | 8/2001 |
| WO | 0162189 A1 | 8/2001 |
| WO | 2001054625 A1 | 8/2001 |
| WO | 0164137 A1 | 9/2001 |
| WO | 0176510 A2 | 10/2001 |
| WO | 0197715 A1 | 12/2001 |
| WO | 0236048 A1 | 5/2002 |
| WO | 0241789 A2 | 5/2002 |
| WO | 0243620 A1 | 6/2002 |
| WO | 0247575 A2 | 6/2002 |
| WO | 02056955 A1 | 7/2002 |
| WO | 02069842 A2 | 9/2002 |
| WO | 02100297 A2 | 12/2002 |
| WO | 03003943 A2 | 1/2003 |
| WO | 03003949 A2 | 1/2003 |
| WO | 03011195 A2 | 2/2003 |
| WO | 03015851 A2 | 2/2003 |
| WO | 03028592 A1 | 4/2003 |
| WO | 03030776 A2 | 4/2003 |
| WO | 03032869 A1 | 4/2003 |
| WO | 03037222 A2 | 5/2003 |
| WO | 03037227 A2 | 5/2003 |
| WO | 03047468 A1 | 6/2003 |
| WO | 03047648 A2 | 6/2003 |
| WO | 03088873 A1 | 10/2003 |
| WO | 03094793 A1 | 11/2003 |
| WO | 03094797 A1 | 11/2003 |
| WO | 03096932 A1 | 11/2003 |
| WO | 2004006803 A1 | 1/2004 |
| WO | 2004006804 A1 | 1/2004 |
| WO | 2004014256 A1 | 2/2004 |
| WO | 2004019817 A1 | 3/2004 |
| WO | 2004021922 A2 | 3/2004 |
| WO | 2004023980 A2 | 3/2004 |
| WO | 2004019811 A9 | 4/2004 |
| WO | 2004026117 A2 | 4/2004 |
| WO | 2004041126 A1 | 5/2004 |
| WO | 2004043293 A2 | 5/2004 |
| WO | 2004047681 A1 | 6/2004 |
| WO | 2004058106 A2 | 8/2004 |
| WO | 2004066876 A1 | 8/2004 |
| WO | 2004082536 A1 | 9/2004 |
| WO | 2004089250 A1 | 10/2004 |
| WO | 2004089253 A1 | 10/2004 |
| WO | 2004093728 A2 | 11/2004 |
| WO | 2004105651 A1 | 12/2004 |
| WO | 2005002466 A2 | 1/2005 |
| WO | 2005004753 A1 | 1/2005 |
| WO | 2005009285 A2 | 2/2005 |
| WO | 2005011534 A1 | 2/2005 |
| WO | 2005011535 A2 | 2/2005 |
| WO | 2005023155 A1 | 3/2005 |
| WO | 2005027790 A1 | 3/2005 |
| WO | 2005046528 A1 | 5/2005 |
| WO | 2005046529 A1 | 5/2005 |
| WO | 2005048883 A1 | 6/2005 |
| WO | 2005065585 A1 | 7/2005 |
| WO | 2005084595 A1 | 9/2005 |
| WO | 2005087140 A1 | 9/2005 |
| WO | 2005096993 A1 | 10/2005 |
| WO | 2006005015 A2 | 1/2006 |
| WO | 2006009690 A1 | 1/2006 |

(56) References Cited

FOREIGN PATENT DOCUMENTS

| | | | |
|---|---|---|---|
| WO | 2006027499 | A2 | 3/2006 |
| WO | 2005062980 | A3 | 5/2006 |
| WO | 2007035471 | A2 | 3/2007 |
| WO | 2005102015 | A3 | 4/2007 |
| WO | 2006138391 | A2 | 4/2007 |
| WO | 2007044285 | A2 | 4/2007 |
| WO | 2007058847 | A2 | 5/2007 |
| WO | 2007092354 | A2 | 8/2007 |
| WO | 2007097983 | A2 | 8/2007 |
| WO | 2007053243 | A2 | 9/2007 |
| WO | 2007033093 | A2 | 1/2008 |
| WO | 2010042950 | A2 | 4/2010 |
| WO | 2010098857 | A1 | 9/2010 |
| WO | 2012116368 | A2 | 8/2012 |
| WO | 2012162228 | A1 | 11/2012 |
| WO | 2013009975 | A1 | 1/2013 |
| WO | 2013028387 | A2 | 2/2013 |
| WO | 2013074671 | A1 | 5/2013 |
| WO | 2013096545 | A1 | 6/2013 |
| WO | 2016126511 | A2 | 8/2016 |
| WO | 2019035966 | A1 | 2/2019 |

OTHER PUBLICATIONS

US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Knudsen et al., "Catheter-implanted prosthetic heart valves." Int'l J. of Art. Organs, 16(5): 253-262, May 1993.
Kort et al., "Minimally Invasive Aortic Valve Replacement: Echocardiographic and Clinical Results." Am. Heart J., 142(3): 476-481, Sep. 2001.
Lawrence et al., "Percutaneous Endovascular Graft: Experimental Evaluation," Radiology, 163(2): 357-60 (May 1987).
Levi et al., "Future of Interventional Cardiology in Pediactrics." Current Opinion in Cardiol., 18:79-90 (2003).
Levy, "*Mycobacterium chelonei* Infection of Porcine Heart Valves." The New England Journal of Medicine, Washington DC, 297(12), Sep. 22, 1977.
Love et al., The Autogenous Tissue Heart Valve: Current Status. Journal of Cardiac Surgery, 6(4): 499-507, Mar. 1991.
Lutter et al., "Percutaneous Aortic Valve Replacement: An Experimental Study. I. Studies on Implantation." J. of Thoracic and Cardio. Surg., 123(4): 768-776, Apr. 2002.
Magovern et al., "Twenty-five-Year Review of the Magovern-Cromie Sutureless Aortic Valve." Ann. Thorac. Surg., 48: S33-4 (1989).
Maraj et al., Evaluation of Hemolysis in Patients with Prosthetic Heart Valves, Clin. Cardiol. 21, 387-392 (1998).
McKay et al., "The Mansfield Scientific Aortic Valvuloplasty Registry: Overview of Acute Hemodynamic Results and Procedural Complications." J. Am. Coll. Cardiol. 17(2): 485-91 (Feb. 1991).
Mirich et al., "Percutaneously Placed Endovascular Glalls for Aortic Aneurysms: Feasibility Study." Radiology, 170: 1033-1037 (1989).
Moazami et al., "Transluminal Aortic Valve Placement: A Feasibility Study With a Newly Designed Collapsiable Aortic Valve," ASAIO J. vol. 42:5, pp. M383-85 (Sep./Oct. 1996).
Moulopoulos et al., "Catheter-Mounted Aortic Valves." Annals of Thoracic Surg., 11(5): 423-430, May 1971.
Paniagua et al., "Heart Watch." Texas Heart Institute. Edition: 8 pages, Spring, 2004.
Paniagua et al., "Percutaneous Heart Valve in the Chronic in Vitro Testing Model." Circulation, 106: e51-e52, Sep. 17, 2002.
Parodi et al., "Transfemoral Intraluminal Graft Implantation for Abdominal Aortic Aneurysms." Ann. Vase. Surg., 5(6):491-9 (1991).
Pavcnik et al., "Percutaneous Bioprosthetic Venous Valve: A Long-term Study in Sheep." J. of Vascular Surg., 35(3):598-603, Mar. 2002.

Pavcnik et al., "Development and Initial Experimental Evaluation of a Prosthetic Aortic Valve for Transcatheter Placement." Radiology 183:151-54 (1992).
Pavcnik, et al., "Aortic and venous valve for percutaneous insertion," Min. Invas. Ther. & Allied Technol. 9(3/4) 287-292 (2000).
Phillips et al., "A Temporary Catheter-Tip Aortic Valve: Hemodynamic Effects on Experimental Acute Aortic Insufficiency." Annals of Thoracic Surg., 21(2): 134-136, Feb. 1976.
Printz, et al., "Let the Blood Circulate." Sulzer Tech. Rev. Apr. 1999.
U.S. Appl. No. 60/553,945 to White.
Raillat et al., "Treatment of Iliac Artery Stenosis with the Wallstent Endoprosthesis." AJR 154(3):613-6 (Mar. 1990).
Remadi et al., "Preliminary results of 130 aortic valve replacements with a new mechanical bileaflet prosthesis: the Edwards MIRA valve" Interactive Cardiovasc. and Thorac. Surg. 2, 80-83 (2003).
Rosch et al., "Gianturco-Rosch Expandable Z-Stents in the Treatment of Superior Vena Cava Syndrome." Cardiovasc. Intervent. Radiol. 15: 319-327 (1992).
Schurink et al,. "Stent Attachment Site—related Endoleakage after Stent Graft Treatment: An in vitro study of the effects of graft size, stent type, and atherosclerotic wall changes." J. Vasc. Surg., 30(4):658-67 (Oct. 1999).
Seminars in Interventional Cardiology, ed. P.W. Surruys, vol. 5 (2000).
Sochman et al., "Percutaneous Transcatheter Aortic Disc Valve Prosthesis Implantation: A Feasibility Study." Cardiovasc. Intervent. Radiol., 23: 384-388, Sep. 2000.
Southern Lights Biomaterials Homepage, http://www.slv.co.nz/, Jan. 7, 2011.
Stanley et al., "Evaluation of Patient Selection Guidelines for Endoluminal AAA Repair With the Zenith Stent Graft: The Australasian Experience." J. Endovasc. Ther. 8:457-464 (2001).
Stassano, "Mid-term Results of the Valve-on-Valve Technique for Bioprosthetic Failure." European Journal of Cardiothoracic Surgery: vol. 18, 453-457, Oct. 2000.
Steinhoff et al., "Tissue Engineering of Pulmonary Heart Valves on Allogenic Acellular Matrix Conduits." Circulation, 102 [suppl. III]: III-50-III-55 (2000).
Stuart, "In Heart Valves, A Brave, New Non-Surgical World." Start-Up. Feb. 9-17, 2004.
Supplemental Search Report from EP Patent Office, EP Application No. 04815634.3, dated Aug. 19, 2011.
Supplemental Search Report from EP Patent Office, EP Application No. 05758878.2, dated Oct. 24, 2011.
Textbook of Interventional Cardiology, 2d Ed., Chapter 75: Percutaneous Expandable Prosthetic Valves (1994).
Thompson et al., "Endoluminal stent grafting of the thoracic aorta: Initial experience with the Gore Excluder," Journal of Vascular Surgery, 1163-70 (Jun. 2002).
Topol, "Percutaneous Expandable Prosthetic Valves." Textbook of Interventional Cardiology, W.B. Saunders Company, 2: 1268-1276, 1994.
Vahanian et al., "Percutaneous Approaches to Valvular Disease." Circulation, 109:1572-1579, Apr. 6, 2004.
Van Herwerden et al., "Percutaneous Valve Implantation: Back to the Future?" Euro. Heart J., 23(18): 1415-1416, Sep. 2002.
VentureBeatProfiles, Claudio Argento, Jan. 7, 2010, http://venturebeatprofiles.com/person/profile/claudio-argento.
Vossoughi et al., Stent Graft Update (2000)—Kononov, Volodos, and Parodi and Palmaz Stents; Hemobahn Stent Graft.
White et al., "Endoleak as a Complication of Endoluminal Grafting of Abdominal Aortic Aneurysms: Classification, Incidence, Diagnosis, and Management." J. Endovac. Surg., 4:152-168 (1997).
Yoshioka et al., "Self-Expanding Endovascular Graft: An Experimental Study in Dogs." AJR 151: 673-76 (Oct. 1988).
USPTO Case IPR2017-01293, U.S. Pat. No. 8,992,608 B, Oct. 13, 2017.
Zhou et al., "Self-expandable Valved Stent of Large Size: Off-Bypass Implantation in Pulmonary Position." Eur. J. Cardiothorac, 24: 212-216, Aug. 2003.
Gore Excluder Instructions for Use (2002).

(56) References Cited

OTHER PUBLICATIONS

USPTO Case IPR 2017-0006, U.S. Pat. No. 8,992,608 B2, "Final Written Decision" Mar. 23, 2018.
Fluency Vascular Stent Graft Instructions for Use (2003).
International Search Report and Written Opinion dated Aug. 21, 2019 for International Application No. PCT/US2019/032444.
Cribier et al., "Percutaneous Transluminal Valvuloplasty of Acquired Aortic Stenosis in Elderly Patients: An Alternative to Valve Replacement?" The Lancet, 63-7 (Jan. 11, 1986).
Supplemental Search Report from EP Patent Office, EP Application No. 04813777.2, dated Aug. 19, 2011.
Laborde et al., "Percutaneous Implantation of the Corevalve Aortic Valve Prosthesis for Patients Presenting High Risk for Surgical Valve Replacement." EuroIntervention: 472-474, Feb. 2006.
"A Matter of Size." Triennial Review of the National Nanotechnology Initiative, The National Academies Press, Washington DC, v-13, http://www.nap.edu/catalog/11752/a-matter-of-size-triennial-review-of-the-national-nanotechnology, 2006.
"Heart Valve Materials—Bovine (cow)." Equine & Porcine Pericardium, Maverick Biosciences Pty. Lt, http://maverickbio.com/biological-medical-device-materials.php?htm. 2009.
"Pericardial Heart Valves." Edwards Lifesciences, Cardiovascular Surgery FAQ, http://www.edwards.com/products/cardiovascularsurgeryfaq.htm, Nov. 14, 2010.
Allen et al., "What are the characteristics of the ideal endovascular graft for abdominal aortic aneurysm exclusion?" J. Endovasc. Surg., 4(2):195-202 (May 1997).
Andersen et al. "Transluminal catheter implantation of a new expandable artificial cardiac valve (the stent—valve) in the aorta and the beating heart of closed chest pigs (Abstiact)." Eur. Heart J., 11 (Suppl.): 224a (1990).
Andersen et al., "Transluminal implantation of artificial heart valves. Description of a new expandable aortic valve and initial results with implantation by catheter technique in closed chest pigs." Euro. Heart J., 13:704-708, May 1992.
Atwood et al., "Insertion of Heart Valves by Catheterization." Project Supervised by Prof. S. Muftu of Northeastern University 2001-2002: 36-40, May 30, 2002.
Atwood et al., "Insertion of Heart Valves by Catheterization." The Capstone Design Course Report. MIME 1501-1502. Technical Design Report. Northeastern University, pp. 1-93, Nov. 5, 2007.
Bailey, "Percutaneous Expandable Prosthetic Valves, Textbook of Interventional Cardiology." vol. 2, 2d ed. Eric J. Topol, W.B. Saunders Co. (1994).
Blum et al., "Endoluminal Stent—Grafts for Intrarenal Abdominal Aortic Aneurysms." New Engl. J. Med., 336:13-20 (1997).
Bodnar et al., "Replacement Cardiac Valves R Chapter 13: Extinct Cardiac Valve Prostheses." Pergamon Publishing Corporation. New York, 307-322, 1991.
Bonhoeffer et al., "Percutaneous Insertion of the Pulmonary Valve." J. Am. Coll. Cardiol., 39:1664-9 (2002).
Bonhoeffer et al., "Transcatheter Implantation of a Bovine Valve in Pulmonary Position: A Lamb Study." Circulation, 102: 813-16 (2000).
Bonhoeffer, et al., "Percutaneous replacement of pulmonary valve in a right ventricle to pulmonary-artery prosthetic conduit with valve dysfunction." The Lancet, vol. 356,1403-05 (Oct. 21, 2000).
Boudjemline et al., "Percutaneous Implantation of a Biological Valve in the Aorta to Treat Aortic Valve Insufficiency—A Sheep Study." Med Sci. Monit., vol. 8, No. 4: BR113-116, Apr. 12, 2002.
Boudjemline et al., "Percutaneous Implantation of a Valve in the Descending Aorta in Lambs." Euro. Heart J., 23: 1045-1049, Jul. 2002.
Boudjemline et al., "Percutaneous Pulmonary Valve Replacement in a Large Right Ventricular Outflow Tract: An Experimental Study." Journal of the American College of Cardiology, vol. 43(6): 1082-1087, Mar. 17, 2004.
Boudjemline et al., "Percutaneous Valve Insertion: A New Approach?" J. of Thoracic and Cardio. Surg, 125(3): 741-743, Mar. 2003.
Boudjemline et al., "Steps Toward Percutaneous Aortic Valve Replacement." Circulation, 105: 775-778, Feb. 12, 2002.
Couper, "Surgical Aspects of Prosthetic Valve Selection," Overview of Cardiac Surgery for the Cardiologist, Springer-Verlag New York, Inc., 131-145 (1994).
Cribier et al., "Early Experience with Percutaneous Transcatheter Implantation of Heart Valve Prosthesis for the Treatment of End-Stage Inoperable Patients with Calcific Aortic Stenosis." J. of Am. Coll. of Cardio, 43(4): 698-703, Feb. 18, 2004.
Cribier et al., "Percutaneous Transcatheter Implantation of an Aortic Valve Prosthesis for Calcific Aortic Stenosis: First Human Case." Percutaneous Valve Technologies, Inc., 16 pages, Apr. 16, 2002.
Cribier et al., "Percutaneous Transcatheter Implementation of an Aortic Valve Prosthesis for Calcific Aortic Stenosis: First Human Case Description." Circulation, 106: 3006-3008, Dec. 10, 2002.
Cribier et al., "Trans-Cathether Implantation of Balloon-Expandable Prosthetic Heart Valves: Early Results in an Animal Model." Circulation [suppl. II] 104(17) II-552 (Oct. 23, 2001).
Cunanan et al., "Tissue Characterization and Calcification Potential of Commercial Bioprosthetic Heart Valves." Ann. Thorac. Surg., S417-421, May 15, 2001.
Cunliffe et al., "Glutaraldehyde Inactivation of Exotic Animal Viruses in Swine Heart Tissue." Applied and Environmental Microbiology, Greenport, New York, 37(5): 1044-1046, May 1979.
Dake et al., "Transluminal Placement of Endovascular Stent-Grafts for the Treatment of Descending Thoracic Aortic Aneurysms." New Engl. J. of Med., 331(26):1729-34 (1994).
Dalby et al., "Non-Surgical Aortic Valve Replacement" Br. J. Cardiol., 10:450-2 (2003).
Dhasmana, et al., "Factors Associated With Periprosthetic Leakage Following Primary Mitral Valve Replacement: With Special Consideration of Suture Technique." Annals of Thorac. Surg. 35(2), 170-8 (Feb. 1983).
Diethrich, AAA Stent Grafts: Current Developments, J. Invasive Cardiol. 13(5) (2001).
Dolmatch et al., Stent Grafts: Current Clinical Practice (2000)—EVT Endograft and Talent Endoprosthesis.
Dotter, "Transluminally-Placed Coilspring Endarterial Tube Grafts," Investigative Radiology, pp. 329-332 (1969).
Emery et al., "Replacement of the Aortic Valve in Patients Under 50 Years of Age: Long-Term Follow-Up of the St. Jude Medical Prosthesis." Ann. Thorac. Surg., 75:1815-9 (2003).
EP Search Report for EP Application No. 06824992.9, dated Aug. 10, 2011.
Examiner's First Report on AU Patent Application No. 2011202667, dated May 17, 2012.
Ferrari et al., "Percutaneous Transvascular Aortic Valve Replacement with Self-Expanding Stent-Valve Device." Poster from the presentation given at SMIT 2000,12th International Conference. Sep. 5, 2000.
Greenberg, "Abdominal Aortic Endografting: Fixation and Sealing." J. Am. Coll. Surg. 194:1:S79-S87 (2002).
Grossi, "Impact of Minimally Invasive Valvular Heart Surgery: A Case-Control Study." Ann. Thorac. Surg., 71:807-10 (2001).
Helmus, "Mechanical and Bioprosthetic Heart Valves in Biomaterials for Artificial Organs." Woodhead Publishing Limited: 114-162, 2011.
Hijazi, "Transcatheter Valve Replacement: A New Era of Percutaneous Cardiac Intervention Begins." J. of Am. College of Cardio., 43(6): 1088-1089, Mar. 17, 2004.
Hourihan et al., "Transcatheter Umbrella Closure of Valvular and Paravalvular Leaks." JACC, Boston, Massachusetts, 20(6): 1371-1377, Nov. 15, 1992.
Huber et al., "Do Valved Stents Compromise Coronary Flow?" European Journal of Cardio-thoracic Surgery, vol. 25: 754-759, Jan. 23, 2004.
Ing, "Stents: What's Available to the Pediatric Interventional Cardiologist?" Catheterization and Cardiovascular Interventions 57:274-386 (2002).
Ionescu, et al., "Prevalence and Clinical Significance of Incidental Paraprosthetic Valvar Regurgitation: A prospective study using transesophageal echocardiography." Heart, 89:1316-21 (2003).

(56) References Cited

OTHER PUBLICATIONS

Kaiser, et al., "Surgery for Left Ventricle Outflow Obstruction: Aortic Valve Replacement and Myomectomy," Overview of Cardiac Surgery for the Cardiologist. Springer-Verlag New York, Inc., 40-45 (1994).
Kato et al., "Traumatic Thoracic Aortic Aneurysm: Treatment with Endovascular Stent-Grafts." Radiol., 205: 657-662 (1997).
Khonsari et al., "Cardiac Surgery: Safeguards and Pitfalls in Operative Technique." 3d ed., 45-74 (2003).
Carpentier-Edwards PERIMOUNT Bioprosthesis (2003).
International Search Report and Written Opinion dated Nov. 22, 2018 for International Application No. PCT/US2018/000241.

\* cited by examiner

REPLACEMENT HEART VALVE COMMISSURE ASSEMBLY

CROSS-REFERENCE TO RELATED APPLICATIONS

This application claims the benefit of priority under 35 U.S.C. § 119 to U.S. Provisional Application Ser. No. 62/671,520, filed May 15, 2018, the entirety of which is incorporated herein by reference.

TECHNICAL FIELD

The present disclosure pertains to medical devices, and methods for manufacturing and/or using medical devices. More particularly, the present disclosure pertains to commissure assemblies for a replacement heart valve implant.

BACKGROUND

A wide variety of intracorporeal medical devices have been developed for medical use, for example, intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

In a first aspect, a replacement heart valve commissure assembly may comprise: a locking mechanism including a first locking portion spaced apart from a second locking portion in a delivery configuration, wherein the first locking portion is configured to engage with the second locking portion in a deployed configuration, and the first locking portion is longitudinally actuatable relative to the second locking portion between the delivery configuration and the deployed configuration; a first valve leaflet secured to the first locking portion; and a second valve leaflet secured to the first locking portion. A first sleeve portion of the first valve leaflet may be fixedly attached to a first fabric sleeve wrapped around a first leg of the first locking portion, and a second sleeve portion of the second valve leaflet may be fixedly attached to a second fabric sleeve wrapped around a second leg of the first locking portion. The first fabric sleeve may include a first end portion, a second end portion, and an elastic central portion configured to engage the first leg, each of the first end portion, the second portion, and the elastic central portion having a length and a thickness.

In addition or alternatively, and in a second aspect, the first fabric sleeve is configured to shift between a relaxed state and an elongated state when the first fabric sleeve is placed in tension.

In addition or alternatively, and in a third aspect, the elastic central portion of the first fabric sleeve is configured to exert a compressive force on the first leg when the tension is released.

In addition or alternatively, and in a fourth aspect, the length of the elastic central portion of the first fabric sleeve is at least 50% greater in the elongated state than in the relaxed state.

In addition or alternatively, and in a fifth aspect, the thickness of the elastic central portion of the first fabric sleeve is at least 50% less in the elongated state than in the relaxed state.

In addition or alternatively, and in a sixth aspect, the length of the first end portion of the first fabric sleeve changes less than 10% between the relaxed state and the elongated state.

In addition or alternatively, and in a seventh aspect, the length of the second end portion of the first fabric sleeve changes less than 10% between the relaxed state and the elongated state.

In addition or alternatively, and in an eighth aspect, the first leg of the first locking portion and the second leg of the first locking portion define a longitudinally-oriented tissue slot extending through first locking portion. The first sleeve portion of the first valve leaflet and the second sleeve portion of the second valve leaflet may both pass through the longitudinally-oriented tissue slot of the first locking portion.

In addition or alternatively, and in a ninth aspect, a width of the longitudinally-oriented tissue slot is greater than a total thickness of the first sleeve portion of the first valve leaflet, the second sleeve portion of the second valve leaflet, the elastic central portion of the first fabric sleeve in the elongated state, and the elastic central portion of the second fabric sleeve in the elongated state.

In addition or alternatively, and in a tenth aspect, the first sleeve portion of the first valve leaflet is fixedly attached to the first fabric sleeve with one or more stitches of a first filament oriented generally parallel to the first leg of the first locking portion.

In addition or alternatively, and in an eleventh aspect, the second sleeve portion of the second valve leaflet is fixedly attached to the second fabric sleeve with one or more stitches of a second filament oriented generally parallel to the second leg of the first locking portion.

In addition or alternatively, and in a twelfth aspect, a replacement heart valve implant may comprise: an expandable anchor member actuatable between a delivery configuration and a deployed configuration; and a replacement heart valve commissure assembly comprising: a locking mechanism including a first locking portion spaced apart from a second locking portion in a delivery configuration, wherein the first locking portion is configured to engage with the second locking portion in a deployed configuration, and the first locking portion is longitudinally actuatable relative to the second locking portion between the delivery configuration and the deployed configuration; a first valve leaflet secured to the first locking portion; and a second valve leaflet secured to the first locking portion. A first sleeve portion of the first valve leaflet may be fixedly attached to a first fabric sleeve wrapped around a first leg of the first locking portion, and a second sleeve portion of the second valve leaflet may be fixedly attached to a second fabric sleeve wrapped around a second leg of the first locking portion. The first fabric sleeve may include a first end portion, a second end portion, and an elastic central portion configured to engage the first leg, each of the first end portion, the second portion, and the elastic central portion having a length and a thickness. The locking mechanism may be configured to lock the expandable anchor member in the deployed configuration.

In addition or alternatively, and in a thirteenth aspect, the replacement heart valve implant may further comprise a polymeric seal member disposed on an outer surface of the expandable anchor member and attached to a distal end of the expandable anchor member.

In addition or alternatively, and in a fourteenth aspect, the first fabric sleeve and the second fabric sleeve are each formed from a braided material.

In addition or alternatively, and in a fifteenth aspect, at least the elastic central portion of each of the first fabric sleeve and the second fabric sleeve is impregnated with polyurethane.

In addition or alternatively, and in a sixteenth aspect, a method of assembling a replacement heart valve commissure assembly for use in a replacement heart valve implant may comprise: inserting a first sleeve portion of a first valve leaflet and a second sleeve portion of a second valve leaflet through a longitudinally-oriented tissue slot of a first locking portion of a locking mechanism; inserting a first fabric sleeve through the longitudinally-oriented tissue slot under tension in an elongated state between the first sleeve portion of the first valve leaflet and a first leg of the first locking portion, and inserting a second fabric sleeve through the longitudinally-oriented tissue slot under tension in an elongated state between the second sleeve portion of the second valve leaflet and a second leg of the first locking portion; wherein a thickness of an elastic central portion of the first fabric sleeve in the elongated state is reduced compared to the thickness of the elastic central portion of the first fabric sleeve in a relaxed state, and a thickness of an elastic central portion of the second fabric sleeve in the elongated state is reduced compared to the thickness of the elastic central portion of the second fabric sleeve in a relaxed state; and releasing the tension on the first fabric sleeve and the second fabric sleeve such that the elastic central portion of each of the first fabric sleeve and the second fabric sleeve shifts toward the relaxed state and increases in thickness to place the first sleeve portion of the first valve leaflet and the second sleeve portion of the second valve leaflet in compression between the first leg of the first locking portion and the second leg of the first locking portion.

In addition or alternatively, and in a seventeenth aspect, the method may further comprise: wrapping the first fabric sleeve around the first leg of the first locking portion such that the first fabric sleeve overlaps itself adjacent the first sleeve portion of the first valve leaflet to form a first overlapped portion, and wrapping the second fabric sleeve around the second leg of the first locking portion such that the second fabric sleeve overlaps itself adjacent the second sleeve portion of the second valve leaflet to form a second overlapped portion; and fixedly attaching the first overlapped portion of the first fabric sleeve to the first sleeve portion of the first valve leaflet, and fixedly attaching the second overlapped portion of the second fabric sleeve to the second sleeve portion of the second valve leaflet.

In addition or alternatively, and in an eighteenth aspect, the method may further comprise, prior to fixedly attaching: clamping the first overlapped portion of the first fabric sleeve to the first sleeve portion of the first valve leaflet, and clamping the second overlapped portion of the second fabric sleeve to the second sleeve portion of the second valve leaflet.

In addition or alternatively, and in a nineteenth aspect, the first fabric sleeve includes a first end portion and a second end portion disposed on opposing sides of the elastic central portion, a thickness of each of the first end portion and the second end portion changing less than 10% when placed in tension.

In addition or alternatively, and in a twentieth aspect, the first fabric sleeve includes a first end portion and a second end portion disposed on opposing sides of the elastic central portion, a length of each of the first end portion and the second end portion changing less than 10% when placed in tension.

In addition or alternatively, and in a twenty-first aspect, a width of the longitudinally-oriented tissue slot is less than a total thickness of the first sleeve portion of the first valve leaflet, the second sleeve portion of the second valve leaflet, the elastic central portion of the first fabric sleeve in a relaxed state, and an elastic central portion of the second fabric sleeve in a relaxed state.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
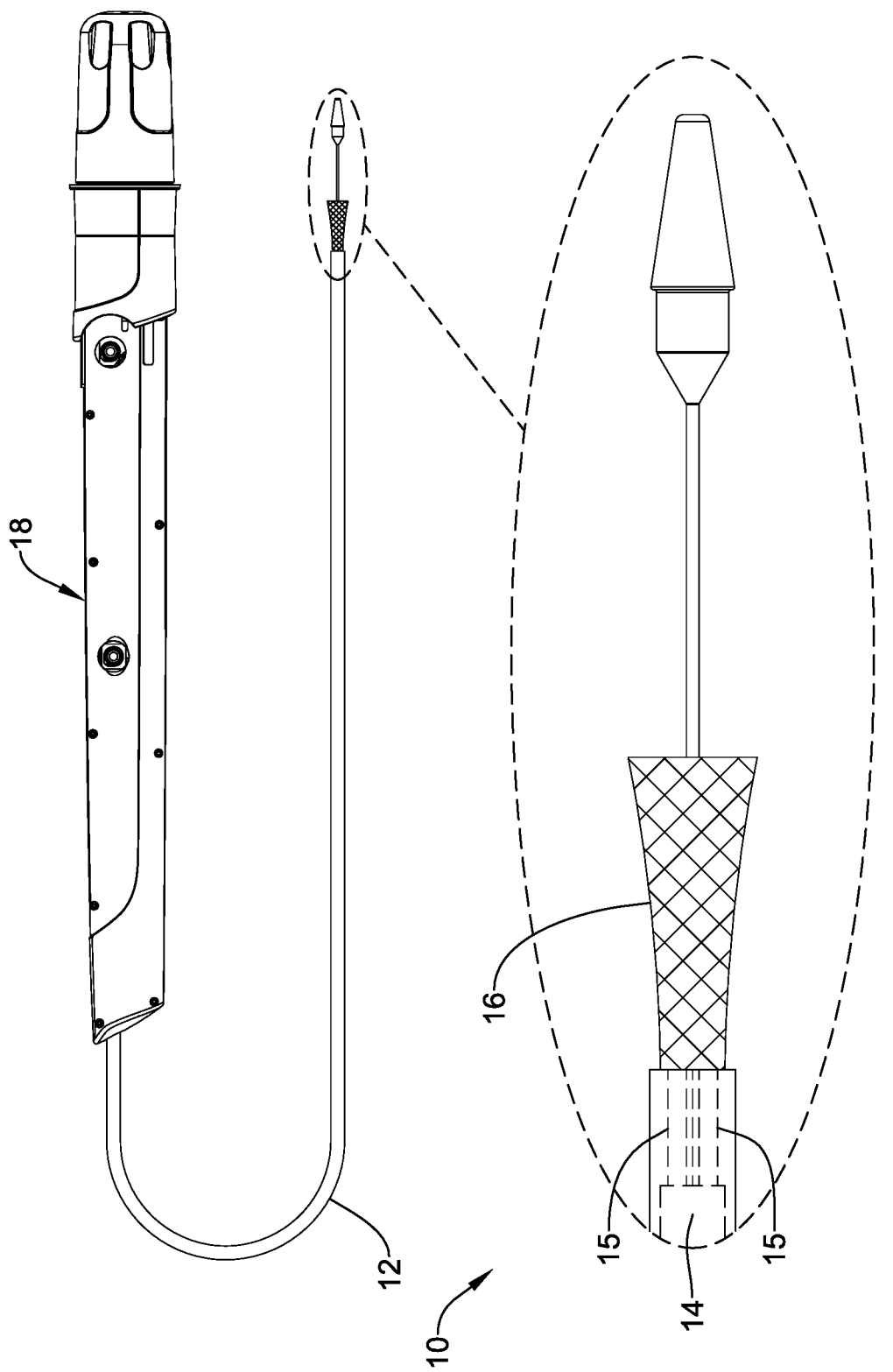
FIG. 1 illustrates an example medical device system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve or the mitral valve can have a serious effect on a human and could lead to serious health condition and/or death if not dealt with properly. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve, replacement mitral valve, etc.). In addition, the devices disclosed herein may deliver the replacement heart valve percutaneously and, thus, may be much less invasive to the patient. The devices disclosed herein may also provide other desirable features and/or benefits as described below.

The figures illustrate selected components and/or arrangements of a medical device system 10, shown schematically in FIG. 1 for example. It should be noted that in any given figure, some features of the medical device system 10 may not be shown, or may be shown schematically, for simplicity. Additional details regarding some of the components of the medical device system 10 may be illustrated in other figures in greater detail. A medical device system 10 may be used to deliver and/or deploy a variety of medical devices and/or implants to one or more locations within the anatomy. In at least some embodiments, the medical device system 10 may include a replacement heart valve delivery system (e.g., a replacement aortic valve delivery system) that can be used for percutaneous delivery of a replacement heart valve implant 16 (e.g. a replacement mitral valve, a replacement aortic valve, etc.) to an area of interest in the anatomy, such as a native heart valve. This, however, is not intended to be limiting as the medical device system 10 may also be used for other interventions including valve repair, valvuloplasty, and the like, or other similar interventions.

FIG. 1 illustrates the medical device system 10 including the replacement heart valve implant 16 configured to be disposed within the area of interest, such as a native heart valve (e.g., a mitral valve, an aortic valve, etc.), wherein the replacement heart valve implant 16 may be disposed within a lumen of the medical device system 10 in a delivery configuration for delivery to the area of interest, where the replacement heart valve implant 16 may be shifted to a deployed configuration. In some embodiments, the medical device system 10 may include an outer sheath 12 having a lumen extending from a proximal portion and/or proximal end of the outer sheath 12 to a distal end of the outer sheath 12. The replacement heart valve implant 16 may be disposed within the lumen of the outer sheath 12 proximate the distal end of the outer sheath 12 in the delivery configuration. In some embodiments, the medical device system 10 may include a handle 18 disposed proximate and/or at the proximal end of the outer sheath 12.

The medical device system 10 may include an inner sheath or catheter 14 disposed within the lumen of the outer sheath 12 and/or slidable with respect to the outer sheath 12 within the lumen of the outer sheath 12. In some embodiments, the handle 18 may be disposed proximate and/or at a proximal end of the inner sheath or catheter 14. In some embodiments, the inner sheath or catheter 14 may be a tubular structure having one or more lumens extending therethrough, the inner sheath or catheter 14 may be a solid shaft, or the inner sheath or catheter 14 may be a combination thereof. In some embodiments, the medical device system 10 may include an actuator element 15 releasably connecting the replacement heart valve implant 16 to the handle 18. For example, the actuator element 15 may extend from the handle 18 to the replacement heart valve implant 16, the replacement heart valve implant 16 being disposed at a distal end of the lumen of the outer sheath 12. The actuator element 15 may extend distally from the inner sheath or catheter 14 to the replacement heart valve implant 16. In some embodiments, the actuator element 15 may be slidably disposed within and/or may extend slidably through the inner sheath or catheter 14.

The handle 18 and/or the actuator element 15 may be configured to manipulate the position of the outer sheath 12 relative to the inner sheath or catheter 14 and/or aid in the deployment of the replacement heart valve implant 16. For example, the inner sheath or catheter 14 and/or the actuator element 15 may be used to move the replacement heart valve implant 16 with respect to the outer sheath 12 of the medical device system 10. In some embodiments, the inner sheath or catheter 14 and/or the actuator element 15 may be advanced distally within the lumen of the outer sheath 12 to push the replacement heart valve implant 16 out the distal end of the outer sheath 12 and/or the medical device system 10 to deploy the replacement heart valve implant 16 within the area of interest (e.g., the native heart valve, etc.). Alternatively, the inner sheath or catheter 14 and/or the actuator element 15 may be held in a fixed position relative to the replacement heart valve implant 16 and the outer sheath 12 may be withdrawn proximally relative to the inner sheath or catheter 14, the actuator element 15, and/or the replacement heart valve implant 16 to deploy the replacement heart valve implant 16 within the area of interest (e.g., the native heart valve, etc.). Some examples of suitable but non-limiting materials for the medical device system 10, the outer sheath 12, the inner sheath or catheter 14, the actuator element 15, the handle 18, and/or components or elements thereof, are described below.

In some embodiments, the medical device system 10 may include a nose cone disposed at a distal end of a guidewire extension tube, wherein the guidewire extension tube may extend distally from the inner sheath or catheter 14 and/or the outer sheath 12. In at least some embodiments, the nose cone may be designed to have an atraumatic shape and/or may include a ridge or ledge that is configured to abut a distal end of the outer sheath 12 during delivery of the replacement heart valve implant 16.

In use, the medical device system 10 may be advanced percutaneously through the vasculature to the area of interest. For example, the medical device system 10 may be advanced through the vasculature and across the aortic arch to a defective heart valve (e.g., aortic valve, mitral valve, etc.). Alternative approaches to treat a defective heart valve are also contemplated with the medical device system 10. During delivery, the replacement heart valve implant 16 may be generally disposed in an elongated and low profile "delivery" configuration within the lumen of the outer sheath 12. Once positioned, the outer sheath 12 may be retracted relative to the replacement heart valve implant 16 to expose the replacement heart valve implant 16. In at least some embodiments, the replacement heart valve implant 16 may be disposed in an "everted" configuration or a partially-everted configuration while disposed within the lumen of the outer sheath 12 and/or immediately upon exposure after retracting the outer sheath 12. In some embodiments, the replacement heart valve implant 16 may be everted in the "delivery" configuration. The "everted" configuration may involve at least a portion of the valve leaflets (discussed below) of the replacement heart valve implant 16 being disposed outside of the expandable anchor member (discussed below) of the replacement heart valve implant 16 during delivery, thereby permitting a smaller radial profile of the replacement heart valve implant 16 and the use of a smaller overall profile of the outer sheath 12 and/or the medical device system 10. In some embodiments, the "delivery" configuration and the "everted" configuration may be substantially similar and/or may be used interchangeably herein.

The replacement heart valve implant 16 may be actuated using the handle 18 and/or the actuator element 15 in order to translate the replacement heart valve implant 16 into a radially expanded and larger profile "deployed" configuration suitable for implantation within the anatomy at the area of interest or the target location. When the replacement heart valve implant 16 is suitably deployed within the anatomy, the outer sheath 12 and/or the medical device system 10 can be removed from the vasculature, leaving the replacement heart valve implant 16 in place in a "released" configuration to function as, for example, a suitable replacement for the native heart valve. In at least some interventions, the replacement heart valve implant 16 may be deployed within the native heart valve (e.g., the native heart valve is left in place and not excised). Alternatively, the native heart valve may be removed and the replacement heart valve implant 16 may be deployed in its place as a replacement.

Disposed within a first lumen of the inner sheath or catheter 14 may be the actuator element 15, which may be used to actuate and/or translate (e.g., expand and/or elongate) the replacement heart valve implant 16 between the "delivery" configuration and the "deployed" configuration. In some embodiments, the actuator element 15 may include or comprise a plurality of actuator elements 15, two actuator elements 15, three actuator elements 15, four actuator elements 15, or another suitable or desired number of actuator elements 15. In some embodiments, each actuator element 15 may be disposed within a separate lumen of the inner sheath or catheter 14. For the purpose of illustration only, the medical device system 10 and the replacement heart valve implant 16 are shown with three actuator elements 15. In such an example, the three actuator elements 15 may be disposed within three separate lumens (e.g., a first lumen, a second lumen, and a third lumen) of the inner sheath or catheter 14, although such a configuration is not required.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the actuator element" may be equally referred to all instances and quantities beyond one of "the at least one actuator element" or "the plurality of actuator elements".

Figure 2:
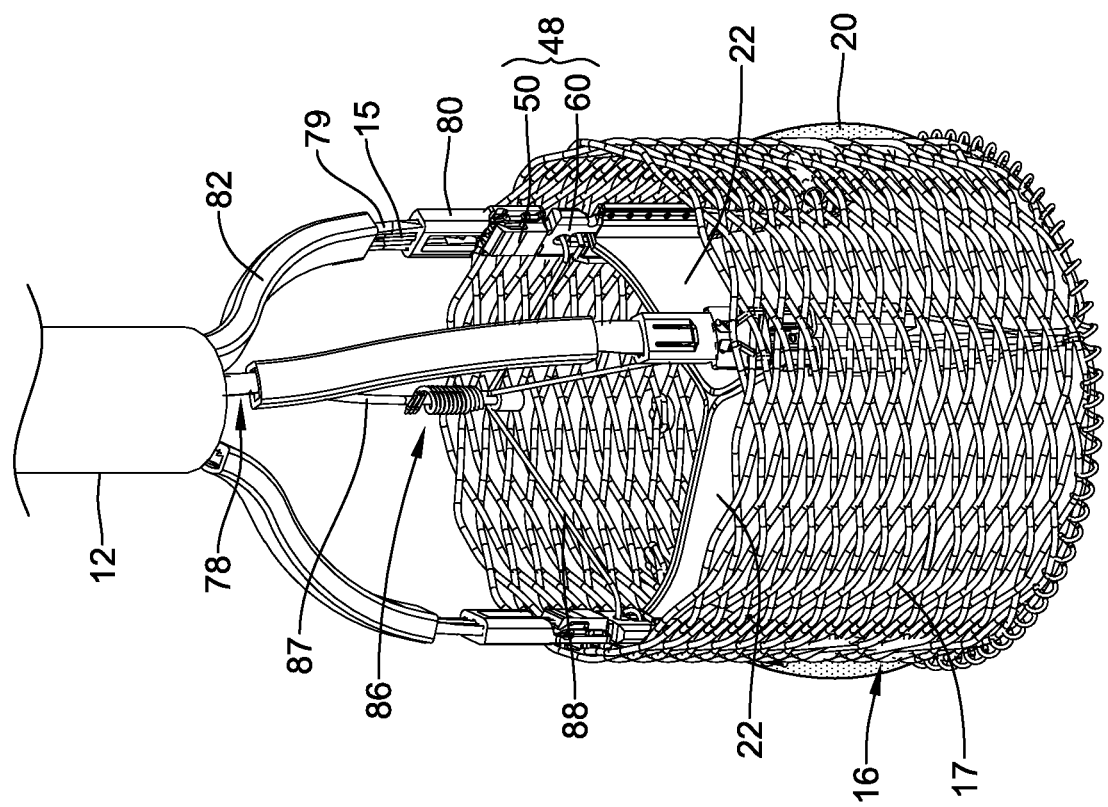
FIG. 2 is a perspective view of an example replacement heart valve implant in a deployed configuration.

FIG. 2 illustrates some selected components of the medical device system 10 and/or the replacement heart valve implant 16, shown in the "deployed" configuration. The replacement heart valve implant 16 may include an expandable anchor member 17 that is reversibly actuatable between the elongated "delivery" configuration and the radially expanded and/or axially shortened "deployed" configuration. In some embodiments, the expandable anchor member 17 may be tubular and defines a lumen extending coaxially along a central longitudinal axis from a distal or inflow end of the expandable anchor member 17 and/or the replacement heart valve implant 16 to a proximal or outflow end of the expandable anchor member 17 and/or the replacement heart valve implant 16.

In some embodiments, the expandable anchor member 17 may comprise an expandable stent structure and/or framework. In some embodiments, the expandable anchor member 17 may comprise a self-expanding braided and/or woven mesh structure made up of one or more filaments disposed and/or interwoven circumferentially about the lumen of the expandable anchor member 17 and/or the replacement heart valve implant 16. Non-self-expanding, mechanically-expandable, and/or assisted self-expanding expandable anchor members are also contemplated. In at least some embodiments, the expandable anchor member 17 may be formed as a unitary structure (e.g., formed from a single filament or strand of wire, cut from a single tubular member, etc.). In some embodiments, the expandable anchor member 17 may define a generally cylindrical outer surface in the deployed configuration. Other configurations are also possible—a cross-section defining a generally elliptical outer surface, for example. Some examples of suitable but non-limiting materials for the replacement heart valve implant 16, the expandable anchor member 17, and/or components or elements thereof, are described below.

Also shown in FIG. 2, but omitted from several other figures in the interest of clarity, the replacement heart valve implant 16 may include a plurality of valve leaflets 22 disposed within the lumen of the replacement heart valve implant 16 and/or the expandable anchor member 17. In some embodiments, the plurality of valve leaflets 22 may be attached and/or secured to the expandable anchor member 17 at a plurality of locations within the lumen of the replacement heart valve implant 16 and/or the expandable anchor member 17. In some embodiments, the plurality of valve leaflets 22 may be attached and/or secured to the expandable anchor member 17 using sutures, adhesives, or other suitable means.

In some embodiments, the plurality of valve leaflets 22 may include or comprise two leaflets, three leaflets, four leaflets, etc. as desired. For example, the plurality of valve leaflets 22 may comprise a first valve leaflet 24, a second valve leaflet 30, a third valve leaflet 36, etc. (e.g., FIGS. 7 and 18), and may be referred to collectively as the plurality of valve leaflets 22 (e.g., FIG. 2). The plurality of valve leaflets 22 of the replacement heart valve implant 16 may be configured to move between an open configuration permitting antegrade fluid flow through the replacement heart valve implant 16 and/or the lumen of the replacement heart valve implant 16 and/or the expandable anchor member 17, and a closed configuration preventing retrograde fluid flow through the replacement heart valve implant 16 and/or the lumen of the replacement heart valve implant 16 and/or the expandable anchor member 17. The plurality of valve leaflets 22 may each have a free edge, wherein the free edges of the plurality of valve leaflets 22 coapt within the replacement heart valve implant 16, the expandable anchor member 17, and/or the lumen extending through the replacement heart valve implant 16 and/or the expandable anchor member 17 in the closed configuration. Additional details regarding the plurality of valve leaflets 22 is provided below.

The replacement heart valve implant 16 may include a replacement heart valve commissure assembly disposed within the lumen of the replacement heart valve implant 16 and/or the expandable anchor member 17. In some embodiments, the replacement heart valve implant 16 may include more than one replacement heart valve commissure assembly. For example, each adjacent pair of valve leaflets 22 may form and/or define one replacement heart valve commissure assembly. Therefore, the number of replacement heart valve commissure assemblies may be directly related to the number of valve leaflets 22 (e.g., three valve leaflets form and/or define three replacement heart valve commissure assemblies, two valve leaflets form and/or define two replacement heart valve commissure assemblies, etc.).

In some embodiments, the replacement heart valve implant 16 and/or the replacement heart valve commissure assembly may include a locking mechanism 48 configured to lock the expandable anchor member 17 in the "deployed" configuration. In some embodiments, the replacement heart valve implant 16 may include or comprise a plurality of locking mechanisms 48, two locking mechanisms 48, three locking mechanisms 48, etc. In some embodiments, each replacement heart valve commissure assembly may correspond to and/or include one corresponding locking mechanism 48. Each locking mechanism 48 may include a first locking portion or a post member 60 secured to the expandable anchor member 17 and configured to engage with a second locking portion or a buckle member 50 secured to the expandable anchor member 17, as will be described in more detail below.

In some embodiments, the actuator element 15 may be configured to releasably engage the locking mechanism 48 and/or reversibly actuate the expandable anchor member 17 and/or the replacement heart valve implant 16 between the "delivery" configuration and the "deployed" configuration and/or the "released" configuration while the actuator element 15 is engaged with the locking mechanism 48. In some embodiments, one actuator element 15 may correspond to, engage with, and/or actuate one locking mechanism 48. In some embodiments, one actuator element 15 may correspond to, engage with, and/or actuate more than one locking mechanism 48. Other configurations are also contemplated.

In some embodiments, the actuator element 15 may include a proximal end and a distal end. In use, the proximal end may be operatively connected to the handle 18, and/or manipulated or otherwise actuated by a user using the handle 18, to reversibly shift the replacement heart valve implant 16 between the "delivery" configuration and the "deployed" configuration. In some embodiments, the actuator element 15 may be axially translatable relative to the first locking portion or post member 60 and/or the second locking portion or buckle member 50 of the replacement heart valve implant 16.

In some embodiments, the actuator element 15 (e.g., each actuator element 15, etc.) includes an elongated rod having a flattened distal portion and a ramp extending longitudinally and/or radially outward from the actuator element 15 such that the ramp has a greater outer extent than the elongated rod. The ramp may be positioned proximate to and/or at a proximal end of the flattened distal portion of the actuator element 15.

In some embodiments, the flattened distal portion of the actuator element 15 may be aligned with and/or releasably coupled to the first locking portion or post member 60. In some embodiments, the flattened distal portion may be slidably received within a longitudinally-oriented passageway of the first locking portion or post member 60, as discussed below. The handle 18 may be configured to actuate and/or translate the actuator element 15 (e.g., each actuator element 15, etc.) relative to the outer sheath 12, the replacement heart valve implant 16, the corresponding locking mechanism(s) 48 (e.g., the plurality of locking mechanisms 48, etc.), and/or the first locking portion or post member 60 in the "delivery" and/or "deployed" configuration.

In some embodiments, the proximal end of the actuator element 15 (each actuator element 15, etc.) may be operatively connected to a central shaft extending distally from the handle 18 within the inner sheath or catheter 14. The central shaft may be actuated and/or translated by the handle 18 and/or a mechanism disposed within the handle 18. In some embodiments, the actuator element 15 (each actuator element 15, etc.) may extend distally from the handle 18 within the inner sheath or catheter 14.

In some embodiments, the actuator element 15 and/or the elongated rod may be generally round, oblong, ovoid, rectangular, polygonal (i.e., two-sided, three-sided, four-sided, five-sided, six-sided, etc.) and/or combinations thereof in shape. Other shapes, both regular and irregular, are also contemplated. In some embodiments, the actuator element 15 may be formed from a single piece of wire, round stock, or other suitable material, as discussed herein. In some embodiments, the actuator element 15 may be formed by further processing the single piece of wire, round stock, or other suitable material, such as by machining, stamping, laser cutting, etc. Some suitable but non-limiting materials for the actuator element 15, the elongated rod, the flattened distal portion, and/or the ramp, for example metallic materials or polymeric materials, are described below.

In some embodiments, the replacement heart valve implant 16 may include a seal member 20 (shown partially cutaway) disposed on and/or around at least a portion of the outer surface of the expandable anchor member 17. In some embodiments, the seal member 20 may be attached and/or secured to the distal or inflow end of the expandable anchor member 17 and/or the replacement heart valve implant 16, and/or the seal member 20 may be attached and/or secured to the plurality of valve leaflets 22 proximate the distal or inflow end of the expandable anchor member 17 and/or the replacement heart valve implant 16. The seal member 20 may be sufficiently flexible and/or pliable to conform to and/or around native valve leaflets and/or the native heart valve in the deployed configuration, thereby sealing an exterior of the replacement heart valve implant 16 and/or the expandable anchor member 17 within and/or against the native heart valve and/or the native valve leaflets and preventing leakage around the replacement heart valve implant 16 and/or the expandable anchor member 17.

In some embodiments, the seal member 20 may include a plurality of layers of polymeric material. Some suitable polymeric materials may include, but are not necessarily limited to, polycarbonate, polyurethane, polyamide, polyether block amide, polyethylene, polyethylene terephthalate, polypropylene, polyvinylchloride, polytetrafluoroethylene, polysulfone, and copolymers, blends, mixtures or combinations thereof. Other suitable polymeric materials are also contemplated, some of which are discussed below.

A pin release assembly 86 may be a linking structure that releasably couples the first locking portion or post member 60 and the actuator element 15. The pin release assembly 86 may include a plurality of release pins 88 that may be joined together via a coiled connection and held to a pin release mandrel 87, for example with a ferrule, a weld, or other attachment means.

During delivery, the replacement heart valve implant 16 and/or the expandable anchor member 17 may be secured at the distal end of the inner sheath or catheter 14 by a plurality of fingers 79 of a coupler 78 coupled with a projecting portion at a proximal end of the second locking portion or buckle member 50 (and being held in place with a slidable collar 80 disposed over the connection) and by the plurality of release pins 88, each release pin 88 securing together the actuator element 15 and the first locking portion or post member 60. The flattened distal portion of the actuator element 15 may include an opening or aperture that can be aligned with an aperture 68 of a transverse distal portion of the first locking portion or post member 60 (described in more detail below). When so aligned, the plurality of release pins 88 can be looped through a coupling aperture extending through the first locking portion or post member 60 proximate the elongated proximal portion 62 and the opening or aperture of the actuator element 15. This releasably secures the actuator element 15 to the first locking portion or post member 60, thereby limiting relative axial movement between the actuator element 15 and the first locking portion or post member 60 and forms a configuration of these structures that can be utilized during delivery of the replacement heart valve implant 16. A guide 82 may be disposed over each of the plurality of fingers 79 proximal of the slidable collar 80 and may serve to keep the plurality of fingers 79 of the coupler 78 associated with their respective actuator element 15 extending adjacent to (and axially slidable relative to) the plurality of fingers 79 of the coupler 78.

After the replacement heart valve implant 16 and/or the expandable anchor member 17 is advanced within the anatomy to the area of interest, the actuator element 15 can be used to actuate the replacement heart valve implant 16 and/or the expandable anchor member 17 to the "deployed" configuration by proximally retracting the actuator element 15 relative to the second locking portion or buckle member 50 and/or the expandable anchor member 17, thereby pulling the first locking portion or post member 60 into engagement with the second locking portion or buckle member 50, as discussed below. Finally, the plurality of release pins 88 can be removed by retracting the pin release mandrel 87 and/or the pin release assembly 86 using the handle 18, thereby uncoupling the actuator element 15 from the first locking portion or post member 60, which allows the replacement heart valve implant 16 to be released from the medical device system 10 in the "released" configuration.

In some embodiments, the first locking portion or post member 60 and the second locking portion or buckle member 50 may be longitudinally movable relative to each other along an inner surface of the expandable anchor member 17 in the "delivery" configuration and/or the "deployed" configuration. In some embodiments, the first locking portion or post member 60 may be non-releasably secured to a distal portion and/or proximate the distal or upstream end of the expandable anchor member 17 along the inner surface of the expandable anchor member 17. In some embodiments, the second locking portion or buckle member 50 may be fixedly secured to a proximal portion and/or proximate the proximal or downstream end of the expandable anchor member 17 against the inner surface of the expandable anchor member 17. The second locking portion or buckle member 50 may be configured to slidably receive at least a portion of the first locking portion or post member 60 therein. Additional discussion regarding the relative motion of these elements is provided below.

Figure 3:
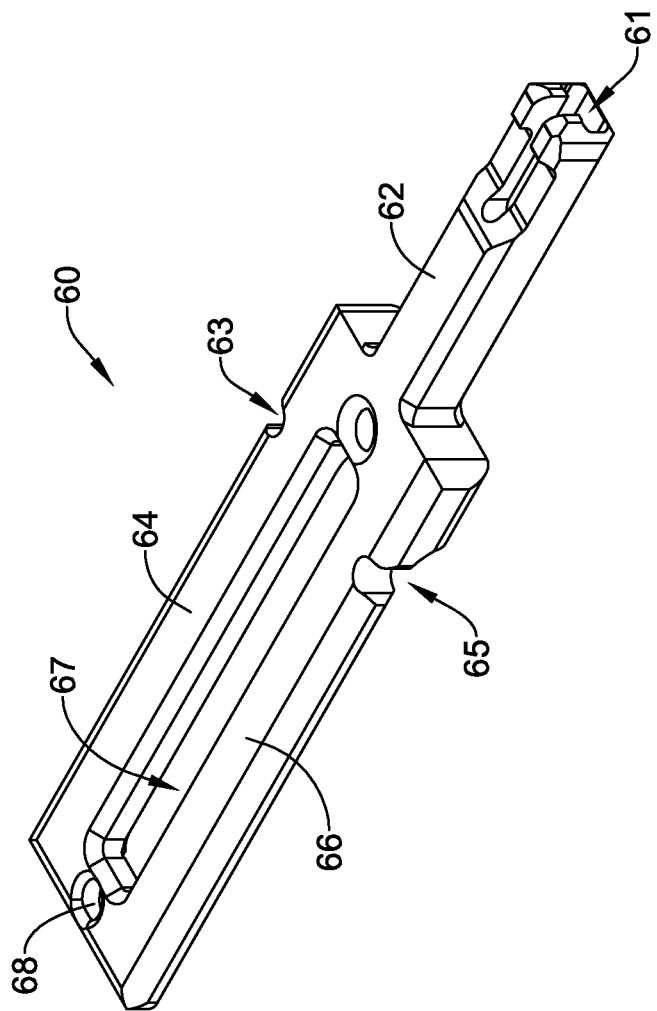
FIG. 3 illustrates an example post member.

FIG. 3 illustrates an example first locking portion or post member 60. In at least some embodiments, the first locking portion or post member 60 may include an elongated proximal portion 62, a first leg 64 fixedly attached to and extending distally from the elongated proximal portion 62, and a second leg 66 fixedly attached to and extending distally from the elongated proximal portion 62. The first locking portion or post member 60 may include a transverse distal portion fixedly attached to and extending laterally and/or circumferentially between a distal end of the first leg 64 and a distal end of the second leg 66. In some embodiments, the first locking portion or post member 60 may be formed as a single unitary structure, wherein the elongated proximal portion 62, the first leg 64, the second leg 66, and the transverse distal portion are integrally formed with each other and/or from a single piece of material. In some embodiments, the transverse distal portion of the first locking portion or post member 60 may include an aperture 68 extending through the transverse distal portion of the first locking portion or post member 60 in a radial direction relative to the central longitudinal axis of the replacement heart valve implant 16 and/or the expandable anchor member 17.

In some embodiments, the elongated proximal portion 62 of the first locking portion or post member 60 may include a longitudinally-oriented passageway 61 extending at least partially through the elongated proximal portion 62 of the first locking portion or post member 60, wherein the flattened distal portion of the actuator element 15 is configured to slidably engage the longitudinally-oriented passageway 61 of the elongated proximal portion 62 of the first locking portion or post member 60. In some embodiments, the longitudinally-oriented passageway 61 may extend completely through the elongated proximal portion 62 of the first locking portion or post member 60. In some embodiments, a longitudinal axis of the longitudinally-oriented passageway 61 and/or the elongated proximal portion 62 of the first locking portion or post member 60 may be arranged generally parallel to the central longitudinal axis of the expandable anchor member 17 and/or the replacement heart valve implant 16.

The longitudinally-oriented passageway 61 may be configured to slidably receive the flattened distal portion of the actuator element 15. The longitudinally-oriented passageway 61 may include an internal cross-sectional shape or profile corresponding to an external cross-sectional shape or profile of the flattened distal portion of the actuator element 15. In some embodiments, the flattened distal portion of the actuator element 15 may be slidably disposed within the longitudinally-oriented passageway 61 and/or may be releasably coupled to the first locking portion or post member 60 by the release pin 88, for example. In some embodiments, at least a portion of the flattened distal portion of the actuator element 15 may extend into the longitudinally-oriented passageway 61 when the flattened distal portion of the actuator element 15 is engaged with the longitudinally-oriented passageway 61 of the elongated proximal portion 62 of the first locking portion or post member 60, for example in the elongated "delivery" configuration and/or the "everted" configuration.

In some embodiments, the first locking portion or post member 60 may be disposed within the lumen of the replacement heart valve implant 16 and/or the expandable anchor member 17 proximate the distal or inflow end of the replacement heart valve implant 16 and/or the expandable anchor member 17 when the expandable anchor member 17 is in the elongated "delivery" configuration and/or the "everted" configuration. In some embodiments, at least a portion of the first locking portion or post member 60 may be disposed distal of the expandable anchor member 17 when the expandable anchor member 17 is in the elongated "delivery" configuration and/or the "everted" configuration.

In some embodiments, the first leg 64 of the first locking portion or post member 60 and the second leg 66 of the first locking portion or post member 60 may be laterally and/or circumferentially spaced apart from each other to define a longitudinally-oriented tissue slot 67 extending through the first locking portion or post member 60 in a radial direction relative to the central longitudinal axis of the replacement heart valve implant 16 and/or the expandable anchor member 17. In some embodiments, a length of the longitudinally-oriented tissue slot 67 may extend and/or may be oriented generally parallel with the central longitudinal axis of the expandable anchor member 17 and/or the replacement heart valve implant 16. The first leg 64 of the first locking portion or post member 60 may include a first lateral recess 63 formed within the first leg 64 proximate a proximal end of the longitudinally-oriented tissue slot 67. The first lateral recess 63 may be formed and/or extend laterally and/or circumferentially into an outer surface of the first leg 64 toward the longitudinally-oriented tissue slot 67. The second leg 66 of the first locking portion or post member 60 may include a second lateral recess 65 formed within the second leg 66 proximate a proximal end of the longitudinally-oriented tissue slot 67. The second lateral recess 65 may be formed and/or extend laterally and/or circumferentially into an outer surface of the second leg 66 toward the longitudinally-oriented tissue slot 67. In at least some embodiments, the first lateral recess 63 and the second lateral recess 65 may face in opposite lateral or circumferential directions.

In some embodiments, the elongated proximal portion 62 of the first locking portion or post member 60 may include a transversely-oriented depression and/or ridge proximate a proximal end of the elongated proximal portion 62. As will be explained further below, the transversely-oriented depression and/or ridge of the elongated proximal portion 62 may be configured to engage a transversely-oriented ridge of the second locking portion or buckle member 50 to lock the replacement heart valve implant 16 and/or the expandable anchor member 17 in the "deployed" configuration.

In some embodiments, the elongated proximal portion 62 of the first locking portion or post member 60 may include a keying or orienting shape formed in and/or extending longitudinally along a length and/or an outer surface of the elongated proximal portion 62 of the first locking portion or post member 60. In some embodiments, the keying or orienting shape may extend along an entire length of the elongated proximal portion 62 of the first locking portion or post member 60. As will become apparent, the keying or orienting shape may serve as an alignment and/or anti-rotation feature with respect to the second locking portion or buckle member 50. For example, the keying or orienting shape may prevent relative rotation between the first locking portion or post member 60 and the second locking portion or buckle member 50 when the elongated proximal portion 62 of the first locking portion or post member 60 is engaged with the second locking portion or buckle member 50. Some suitable but non-limiting materials for the first locking portion or post member 60, for example metallic materials or polymeric materials, are described below.

Figure 4:
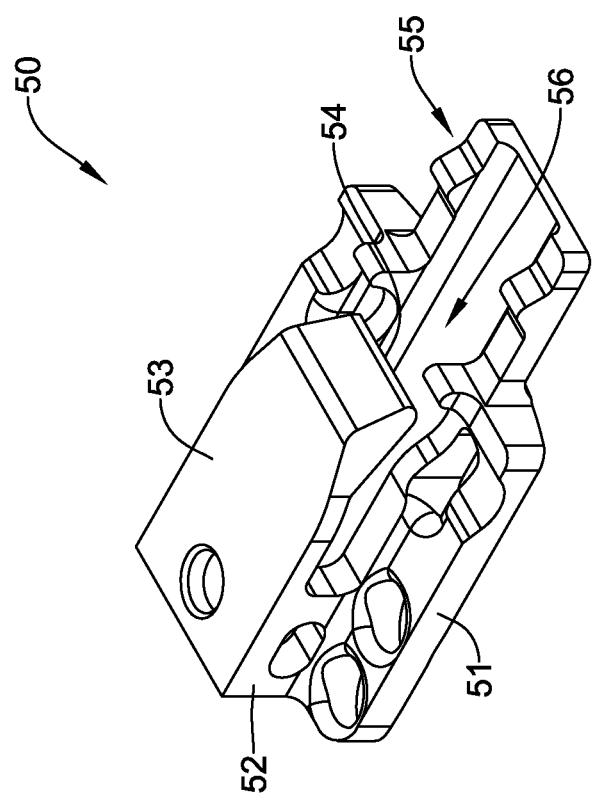
FIG. 4 illustrates an example buckle member.

FIG. 4 illustrates an example second locking portion or buckle member 50. The second locking portion or buckle member 50 may include a base portion 51 having a longitudinal axis extending between a proximal end and a distal end of the second locking portion or buckle member 50. The second locking portion or buckle member 50 may include a body portion 52 fixedly attached to and/or integrally formed with the base portion 51, the body portion 52 defining a longitudinal channel 56 extending through the body portion 52 of the second locking portion or buckle member 50. In at least some embodiments, the longitudinal channel 56 may be oriented substantially parallel with the longitudinal axis of the base portion 51. In some embodiments, at least a part of the body portion 52 may extend away from a distal portion of a top surface of the base portion 51. For example, the body portion 52 may extend radially inward from the base portion 51 relative to the central longitudinal axis of the replacement heart valve implant 16 and/or the expandable anchor member 17.

In some embodiments, the body portion 52 of the second locking portion or buckle member 50 may include a flap portion 53 extending proximally and/or toward the proximal end of the base portion 51 from the body portion 52. In some embodiments, the flap portion 53 may include a transversely-oriented ridge 54 extending toward the base portion 51 and laterally across the base portion 51, such that when the second locking portion or buckle member 50 is viewed along the longitudinal axis of the base portion 51, the transversely-oriented ridge 54 obstructs at least a portion of the longitudinal channel 56. In some embodiments, the body portion 52 and/or the flap portion 53 of the second locking portion or buckle member 50 may include at least one hole or aperture formed therein for attaching a radiopaque marker to the second locking portion or buckle member 50 to aid in visualization of the second locking portion or buckle member 50.

The flap portion 53 may be configured to deflect radially relative to the central longitudinal axis of the expandable anchor member 17 and/or the replacement heart valve implant 16. As will become more evident from the discussion below, the ramp of the actuator element 15 may be configured to deflect the flap portion 53 of the second locking portion or buckle member 50 radially inward as the ramp (and the first locking portion or post member 60 engaged thereto) is longitudinally translated through the longitudinal channel 56 of the body portion 52 of the second locking portion or buckle member 50. In some embodiments, the flap portion 53 may be biased or self-biased toward a neutral position aligned with the body portion 52 and/or may be biased or self-biased into the longitudinal channel 56 and/or toward the base portion 51 of the second locking portion or buckle member 50.

In some embodiments, the second locking portion or buckle member 50 may include a projecting portion 55 at a proximal end of the base portion 51 of the second locking portion or buckle member 50, the projecting portion 55 being configured to releasably attach the replacement heart valve implant 16 to the medical device system 10 and/or the inner sheath or catheter 14. In at least some embodiments, the longitudinal channel 56 may have a keyed, directional, or non-round cross-sectional profile or shape configured to slidably receive the first locking portion or post member 60. The first locking portion or post member 60 may have an external cross-sectional profile or shape corresponding to the keyed, directional, or non-round internal cross-sectional profile or shape of the longitudinal channel 56. For example, the longitudinal channel 56 and/or the projecting portion 55 may include a flat surface corresponding to a flat side of the first locking portion or post member 60. Other corresponding surfaces and/or profiles are also contemplated. As such, the first locking portion or post member 60 may be nonrotatable relative to the second locking portion or buckle member 50 when the elongated proximal portion 62 of the first locking portion or post member 60 is engaged with and/or at least partially disposed within the longitudinal channel 56 of the second locking portion or buckle member 50 and/or when the flat side of the first locking portion or post member 60 is aligned with and/or in facing engagement with the flat surface of the second locking portion or buckle member 50. Some suitable but non-limiting materials for the second locking portion or buckle member 50, for example metallic materials or polymeric materials, are described below.

Briefly returning to FIG. 2, in some embodiments, attachment between the replacement heart valve implant 16 and the inner sheath or catheter 14 may be effected through the use of a coupler 78. The coupler 78 may generally include a base (not shown) that may be attached to a distal end of the inner sheath or catheter 14. Projecting distally from the base is a plurality of fingers 79 (e.g., two fingers, three fingers, four fingers, etc.) that are each configured to engage with the replacement heart valve implant 16 at the projecting portion 55 of the second locking portion or buckle member 50 of the locking mechanism 48. In some embodiments, each of the plurality of fingers 79 may extend from the base and/or the distal end of the inner sheath or catheter 14 to the replacement heart valve implant 16. In some embodiments, each finger 79 may include a collar 80 slidably disposed about its respective finger 79 and the projecting portion 55 of its respective second locking portion or buckle member 50.

During delivery, the replacement heart valve implant 16 may be secured at the distal end of the coupler 78 and/or the inner sheath or catheter 14 by two elongated tines of the finger 79 of the coupler 78 being matingly coupled with the projecting portion 55 of the second locking portion or buckle member 50 by the collar 80, and by the actuator element 15 being coupled to its corresponding first locking portion or post member 60, for example by the release pin 88. When the replacement heart valve implant 16 is advanced within the anatomy to the area of interest, the outer sheath 12 may be translated and/or actuated proximally to expose the replacement heart valve implant 16. Then, the actuator element 15 can be actuated (e.g., proximally retracted) to axially shorten and/or radially expand the replacement heart valve implant 16 and/or the expandable anchor member 17 from the "delivery" configuration toward the "deployed" configuration by proximally retracting and/or translating the actuator element 15 to pull the first locking portion or post member 60 into engagement with the second locking portion or buckle member 50, using the handle 18 for example. After verifying satisfactory placement of the replacement heart valve implant 16, such as by an appropriate imaging technique, the actuator element 15 may each be rotated relative to and decoupled from the first locking portion or post member 60, which allows the distal portion of the actuator element 15 to be pulled proximally out of the second locking portion or buckle member 50, where the ramp subsequently engages the collar 80 and thereby retracts the collar 80 from the two elongated tines and the projecting portion 55. Once the collar 80 has been retracted, the two elongated tines decouple from the projecting portion 55, and the finger 79 of the coupler 78 may be withdrawn from the replacement heart valve implant 16 thereby leaving the replacement heart valve implant 16 (and/or the expandable anchor member 17) in the anatomy at the area of interest in a "released" configuration.

Figure 5:
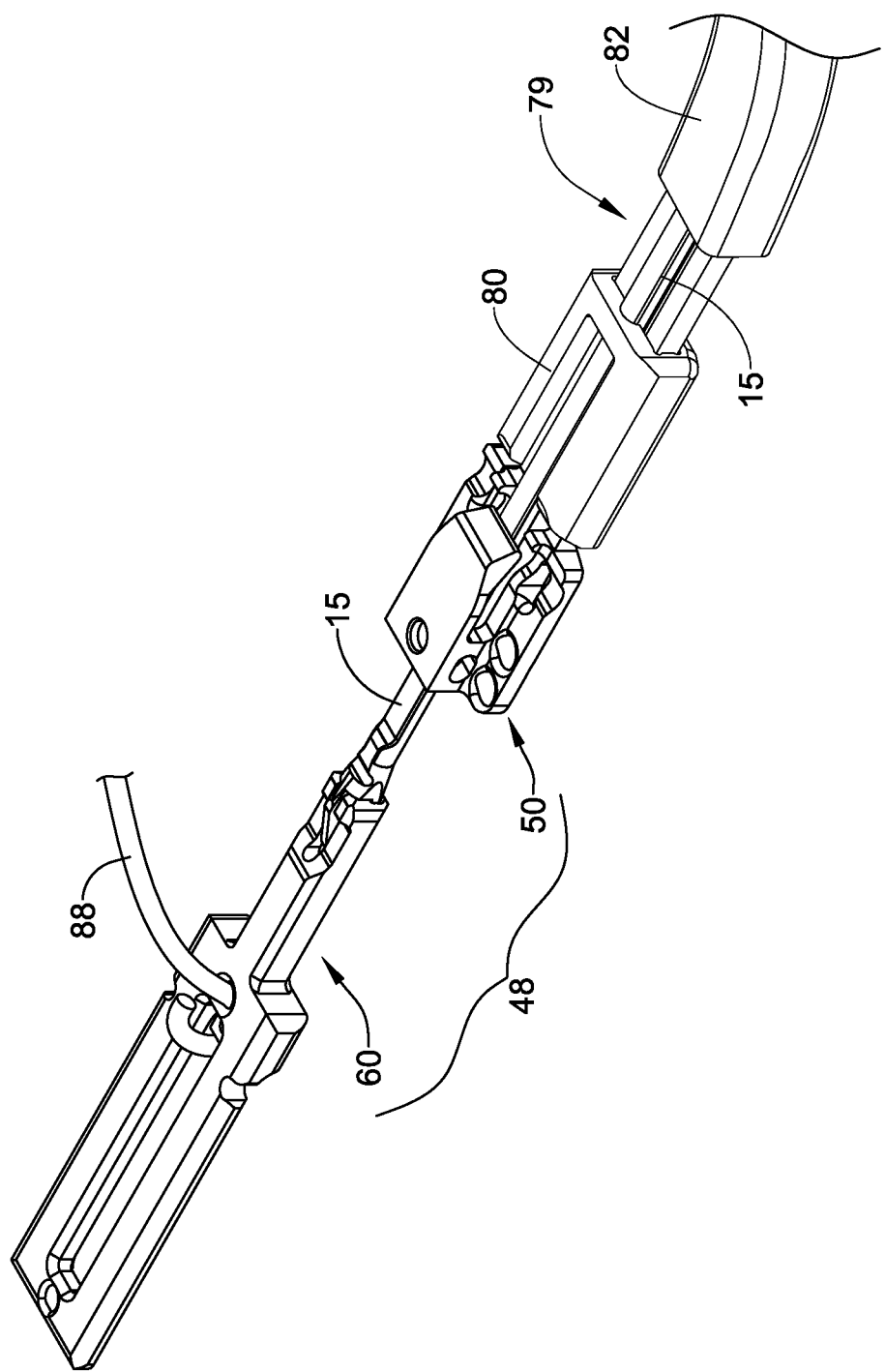
FIG. 5 illustrates selected components of an example replacement heart valve implant associated with an example medical device system in a delivery configuration.
Figure 6:
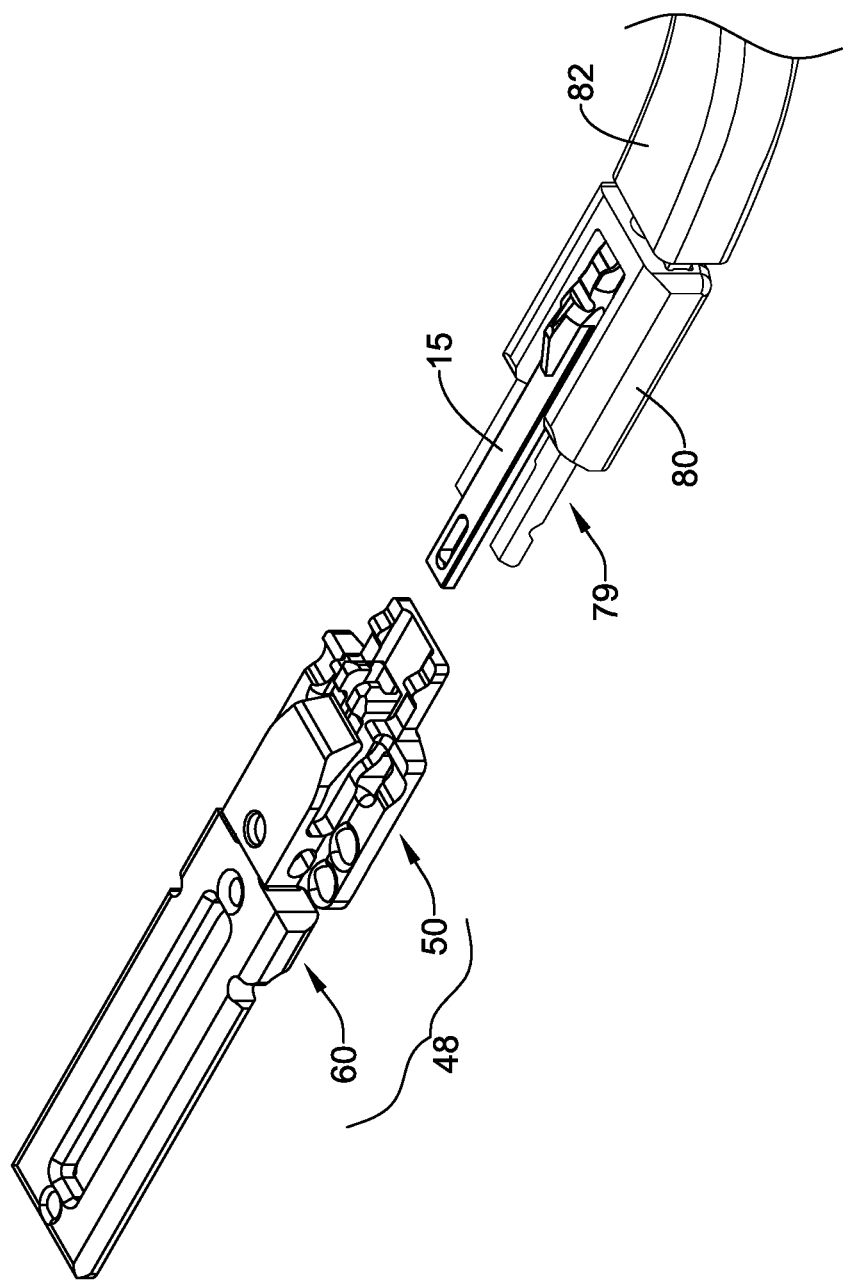
FIG. 6 illustrates selected components of an example replacement heart valve implant associated with an example medical device system in a released configuration.

FIGS. 5-6 illustrate selected components of the locking mechanism 48 configured to reversibly lock the replacement heart valve implant 16 (and/or the expandable anchor member 17) in the "deployed" configuration and/or the "released" configuration, and the general operation of those components. For simplicity and clarity purposes, only one of each actuator element 15, first locking portion or post member 60, second locking portion or buckle member 50, etc. is shown and discussed (the whole replacement heart valve implant 16 is not shown to facilitate understanding of the locking mechanism(s) 48). However, it will be understood that the following discussion may apply equally to any and/or all of the components for which there are more than one within the replacement heart valve implant 16 (i.e., the actuator element 15, the second locking portion or buckle member 50, the first locking portion or post member 60, etc.) and/or the medical device system 10, unless explicitly stated to the contrary.

As seen in FIG. 5, each actuator element 15 extends through a guide 82 adjacent to and surrounding the finger 79 of the coupler 78, through the collar 80, through the second locking portion or buckle member 50, and into engagement with the first locking portion or post member 60. For example, the actuator element 15 (e.g., the plurality of actuator elements 15, etc.) corresponding to each locking mechanism 48 (e.g., the plurality of locking mechanisms 48, etc.) extends longitudinally through the second locking portion or buckle member 50 of its respective locking mechanism 48 in the "delivery" configuration.

The actuator element 15 may be axially and/or slidably translatable through and/or relative to the guide 82, the collar 80, and/or the second locking portion or buckle member 50. The actuator element 15 may be slidable within the longitudinally-oriented passageway 61 of the first locking portion or post member 60. As discussed above, the flattened distal portion of the actuator element 15 may be configured to slidably engage and/or extend into the longitudinally-oriented passageway 61 of the first locking portion or post member 60.

The release pin 88 may extend through the coupling aperture extending through the first locking portion or post member 60 proximate the elongated proximal portion 62, and the opening or aperture through the flattened distal portion of the actuator element 15 to releasably couple the flattened distal portion of the actuator element 15 to the first locking portion or post member 60 in the "delivery" configuration. As can be appreciated, a proximal end of the first locking portion or post member 60 and a distal end of the second locking portion or buckle member 50 may be longitudinally separated and/or spaced apart in the "delivery" configuration (as seen in FIG. 5, for example). In at least some embodiments, the first locking portion or post member 60 may be longitudinally actuatable and/or translatable relative to the second locking portion or buckle member 50 in the "delivery" configuration, and/or between the "delivery" configuration and the "deployed" configuration.

When the replacement heart valve implant 16 reaches the area of interest within the anatomy, a clinician can actuate (e.g., proximally retract) the actuator element 15, for example using the handle 18, thereby moving and/or translating the proximal end of the first locking portion or post member 60 toward the distal end of the second locking portion or buckle member 50 and into the longitudinal channel 56 of the second locking portion or buckle member 50 in order to axially shorten and/or radially expand the expandable anchor member 17 and/or the replacement heart valve implant 16 towards the "deployed" configuration. Ultimately, the actuator element 15 can be retracted sufficiently far enough to translate the actuator element 15 past the flap portion 53 of the second locking portion or buckle member 50 as the ramp passes through the longitudinal channel 56 of the second locking portion or buckle member 50, thereby permitting the ramp of the actuator element 15 to deflect the flap portion 53 of the second locking portion or buckle member 50 radially inward as the ramp (and the first locking portion or post member 60 engaged thereto) is longitudinally translated through the longitudinal channel 56 of the body portion 52 of the second locking portion or buckle member 50. In at least some embodiments, the first locking portion or post member 60 may be longitudinally actuatable and/or translatable relative to the second locking portion or buckle member 50 between the "delivery" configuration and the "deployed" configuration.

As the first locking portion or post member 60 is actuated and/or translated proximally through and/or relative to the second locking portion or buckle member 50, the transversely-oriented depression and/or ridge proximate the proximal end of the elongated proximal portion 62 engages the transversely-oriented ridge 54 of the second locking portion or buckle member 50 to lock the expandable anchor member 17 and/or the replacement heart valve implant 16 into the "deployed" configuration. Engagement of the transversely-oriented depression and/or ridge proximate the proximal end of the elongated proximal portion 62 and the transversely-oriented ridge 54 of the second locking portion or buckle member 50 limit or prevent distal movement and/or axial translation of the first locking portion or post member 60 relative to the second locking portion or buckle member 50 in the "deployed" configuration after the actuator element 15 has been disengaged from the locking mechanism 48 and/or the first locking portion or post member 60. Following locking of the expandable anchor member 17 and/or the replacement heart valve implant 16 in the "deployed" configuration, positioning of the replacement heart valve implant 16 may be verified using a suitable imaging technique.

In some embodiments and/or some procedures, it may be desirable to remove and/or reposition the replacement heart valve implant 16 and/or expandable anchor member 17. To do so, a clinician may urge and/or translate the actuator element 15 in a second (e.g., distal) direction to extend and/or elongate the expandable anchor member 17 back towards the "delivery" configuration. Axial translation of the actuator element 15 in the second (e.g., distal) direction relative to the locking mechanism 48 (e.g., the first locking portion or post member 60 and/or the second locking portion or buckle member 50) may slidably engage the ramp of the actuator element 15 with the flap portion 53 and/or the transversely-oriented ridge 54 the second locking portion or buckle member 50, thereby deflecting the flap portion 53 of the second locking portion or buckle member 50 away from the longitudinal channel 56 of the second locking portion or buckle member 50 and/or the actuator element 15 and/or radially inward relative to the central longitudinal axis of the expandable anchor member 17, and permitting the first locking portion or post member 60 to pass back through and/or out of the longitudinal channel 56 of the second locking portion or buckle member 50.

Upon verification of proper positioning at the area of interest, the release pin(s) 88 may be withdrawn from the coupling aperture extending through the first locking portion or post member 60 proximate the elongated proximal portion 62, and the opening or aperture through the flattened distal portion of the actuator element 15. Once the actuator element 15 has been disengaged and/or detached from the first locking portion or post member 60, and the ramp has been axially translated away from the locking mechanism 48 (e.g., the first locking portion or post member 60 and/or the second locking portion or buckle member 50), and the replacement heart valve implant 16 and/or the expandable anchor member 17 in the "deployed" configuration, further actuation and/or retraction of the actuator element 15 may cause the ramp of the actuator element 15 to engage the collar 80 and pull/slide the collar 80 proximally along the finger 79 while further withdrawing the actuator element 15 from the first locking portion or post member 60. In doing so, the two elongated tines of the finger 79 may be exposed and decoupled from the projecting portion 55 of the second locking portion or buckle member 50, as seen in FIG. 6. Withdrawal of the actuator element 15 completely from the longitudinally-oriented passageway 61 of the first locking portion or post member 60 releases the expandable anchor member 17 and/or the replacement heart valve implant 16 and leaves the replacement heart valve implant 16 disposed at the area of interest in the "released" configuration.

Figure 7:
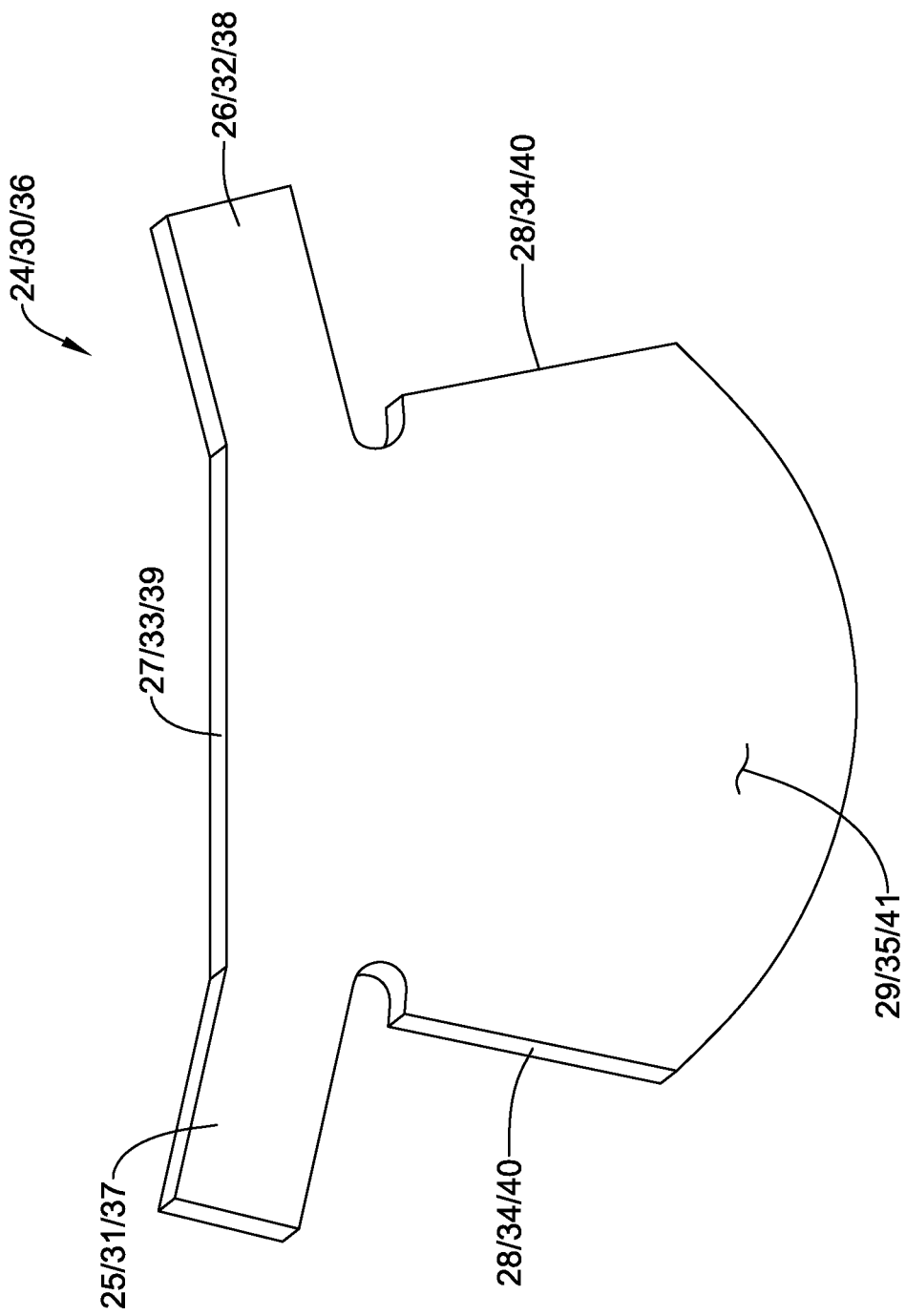
FIG. 7 illustrates an example valve leaflet.

FIG. 7 illustrates an example valve leaflet (e.g., a first valve leaflet 24, a second valve leaflet 30, a third valve leaflet 36) of the plurality of valve leaflets 22. In some embodiments, the first valve leaflet 24, the second valve leaflet 30, and/or the third valve leaflet 36 may each include a body portion 29/35/41 (respectively), a first sleeve portion 25/31/37 (respectively), a second sleeve portion 26/32/38 (respectively) opposite the first sleeve portion 25/31/37 (respectively) relative to the body portion 29/35/41 (respectively), and a free edge 27/33/39 (respectively) extending between the first sleeve portion 25/31/37 (respectively) and the second sleeve portion 26/32/38 (respectively). The free edges 27/33/29 may coapt with each other in the closed configuration to prevent retrograde fluid flow through the replacement heart valve implant 16, and may move radially outwardly relative to the central longitudinal axis and/or the expandable anchor member 17 in the open configuration to permit antegrade fluid flow through the replacement heart valve implant 16.

The first valve leaflet 24, the second valve leaflet 30, and/or the third valve leaflet 36 may each further include a front surface, a back surface, and side edges 28/34/40 (respectively). In some embodiments, the front surface may have a different texture than the back surface. In at least some embodiments, the front surface of the first valve leaflet 24, the front surface of the second valve leaflet 30, and the front surface of the third valve leaflet 36 may each face radially inwardly toward the central longitudinal axis. In some embodiments, the first valve leaflet 24, the second valve leaflet 30, and/or the third valve leaflet 36 may each define notches along the side edges 28/34/40 (respectively) adjacent to the first sleeve portion 25/31/37 (respectively) and the second sleeve portion 26/32/38 (respectively). Some examples of suitable but non-limiting materials for the plurality of valve leaflets 22 (e.g., the first valve leaflet 24, the second valve leaflet 30, the third valve leaflet 36, etc.) may include bovine pericardial, polymeric materials, or other suitably flexible biocompatible materials.

Figure 8:
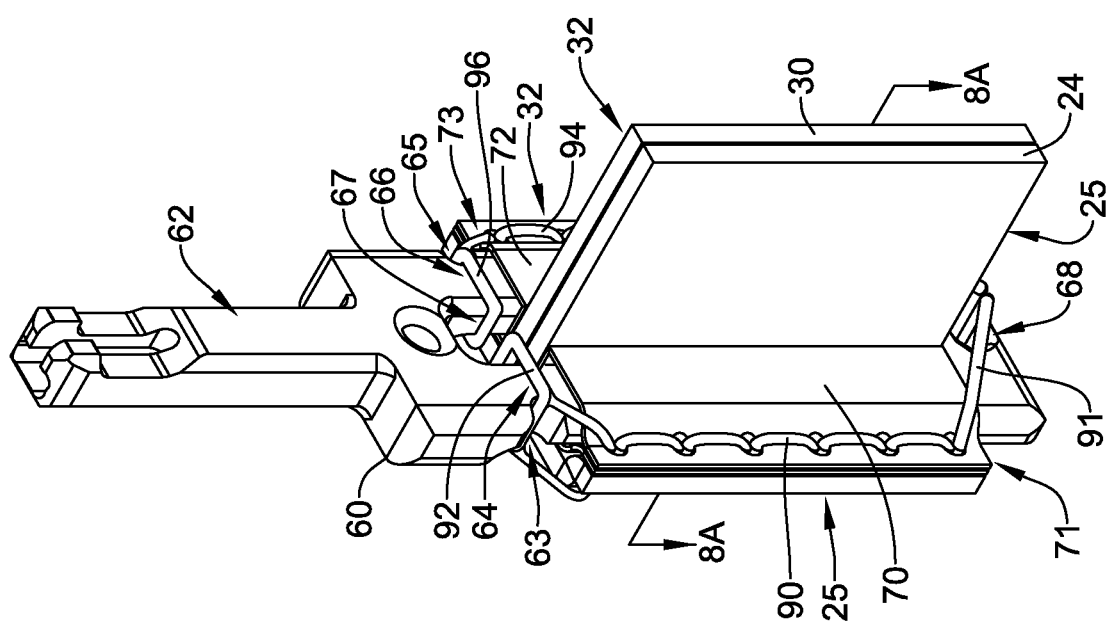
FIG. 8 is a front perspective view illustrating selected components of a replacement heart valve commissure assembly.
Figure 8A:
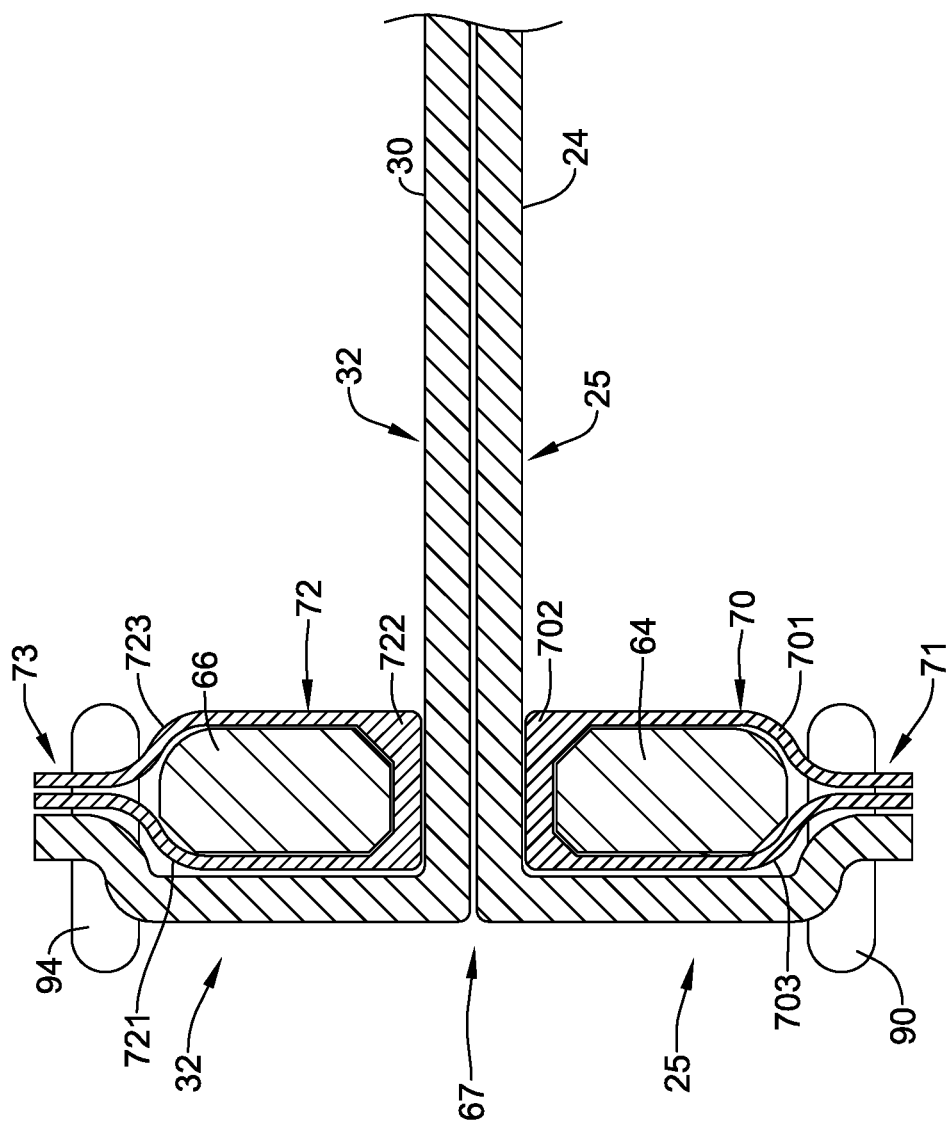
FIG. 8A is a section view of the selected components of FIG. 8 taken along the line 8A-8A.
Figure 9:
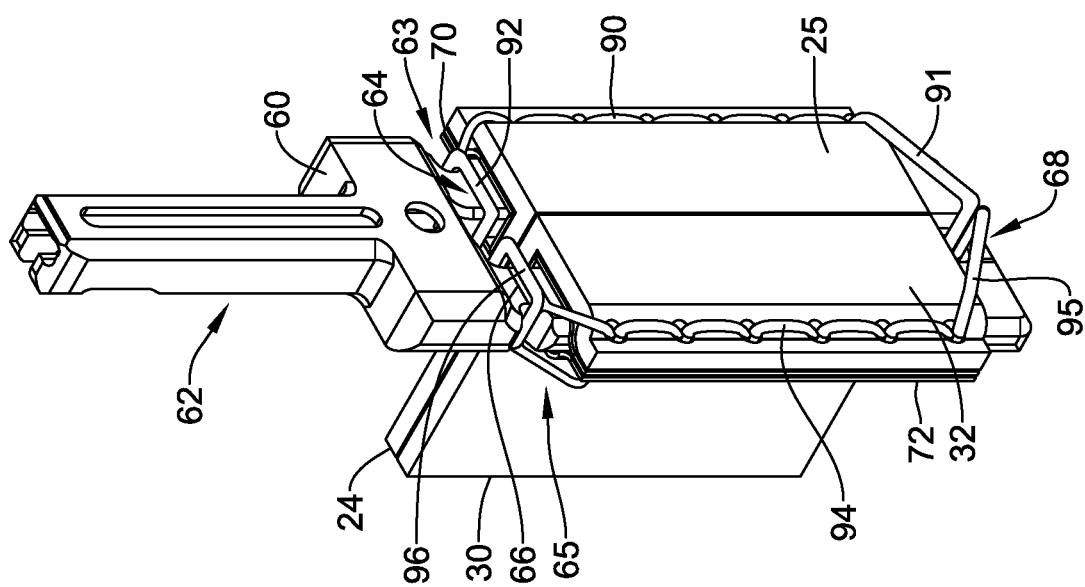
FIG. 9 a rear perspective view illustrating the selected components of the replacement heart valve commissure assembly of FIG. 8.

FIGS. 8, 8A, and 9 illustrate different views of selected elements of the replacement heart valve commissure assembly of the disclosure. In some embodiments, the replacement heart valve commissure assembly includes the first valve leaflet 24 secured to the first locking portion or post member 60 and the second valve leaflet 30 secured to the first locking portion or post member 60. As above, the description herein is written using these exemplary features, but the numerical identifiers (e.g., first, second, etc.) may be changed as necessary for other/additional instances of this or similar features, as will be apparent to the skilled practitioner.

In some embodiments, the first sleeve portion 25 of the first valve leaflet 24 and the second sleeve portion 32 of the second valve leaflet 30 may both pass through the longitudinally-oriented tissue slot 67 extending through the first locking portion or post member 60 between the first leg 64 of the first locking portion or post member 60 and the second leg 66 of the first locking portion or post member 60. To improve clarity, portions of the first valve leaflet 24 and the second valve leaflet 30 (e.g., the body portion 29/35/41, the side edges 28/34/40, etc.) are not shown. The first sleeve portion 25 of the first valve leaflet 24 may be fixedly attached to a first fabric sleeve 70 wrapped around the first leg 64 of the first locking portion or post member 60 by a first filament 90. The second sleeve portion 32 of the second valve leaflet 30 may be fixedly attached to a second fabric sleeve 72 wrapped around the second leg 66 of the first locking portion or post member 60 by a second filament 94.

Shown only in FIG. 8A in the interest of clarity, the first fabric sleeve 70 may include a first end portion 701, a second end portion 703, and an elastic central portion 702. The first end portion 701 of the first fabric sleeve 70 and the second end portion 703 of the first fabric sleeve 70 may be disposed on opposite sides of the elastic central portion 702 of the first fabric sleeve 70. Similarly, the second fabric sleeve 72 may include a first end portion 721, a second end portion 723, and an elastic central portion 722. The first end portion 721 of the second fabric sleeve 72 and the second end portion 723 of the second fabric sleeve 72 may be disposed on opposite sides of the elastic central portion 722 of the second fabric sleeve 72. Additional details related hereto are discussed below with respect to FIGS. 10 and 11.

The first fabric sleeve 70 may be wrapped around the first leg 64 of the first locking portion or post member 60 such that the first fabric sleeve 70 overlaps itself adjacent the first sleeve portion 25 of the first valve leaflet 24 to form a first overlapped portion 71 of the first fabric sleeve 70. The second fabric sleeve 72 may be wrapped around the second leg 66 of the first locking portion or post member 60 such that the second fabric sleeve 72 overlaps itself adjacent the second sleeve portion 32 of the second valve leaflet 30 to form a second overlapped portion 73 of the second fabric sleeve 72.

In some embodiments, the first sleeve portion 25 of the first valve leaflet 24 may be fixedly attached to the first fabric sleeve 70 with one or more stitches of the first filament 90 oriented generally parallel to the first leg 64 of the first locking portion or post member 60. In some embodiments, the second sleeve portion 32 of the second valve leaflet 30 may be fixedly attached to the second fabric sleeve 72 with one or more stitches of the second filament 94 oriented generally parallel to the second leg 66 of the first locking portion or post member 60. Other configurations, including quantity of filaments and/or orientation of filaments are also contemplated. Additionally, other joining means (e.g., staples, rivets, adhesives, etc.), and varying quantities thereof, for fixedly attaching the first sleeve portion 25 to the first fabric sleeve 70 and/or fixedly attaching the second sleeve portion 32 to the second fabric sleeve 72 are also contemplated.

In some embodiments, the first filament 90 includes a first distal section 91 passing through the aperture 68 extending through the transverse distal portion of the first locking portion or post member 60, and the second filament 94 includes a second distal section 95 passing through the aperture 68 extending through the transverse distal portion of the first locking portion or post member 60. In some embodiments, the first filament 90 includes a first proximal section 92 wrapped around the first leg 64 of the first locking portion or post member 60 proximal of the first fabric sleeve 70, and the second filament 94 includes a second proximal section 96 wrapped around the second leg 66 of the first locking portion or post member 60 proximal of the second fabric sleeve 72. In some embodiments, at least a portion of the first proximal section 92 of the first filament 90 is positioned within the first lateral recess 63 formed within the first leg 64 proximal of the first fabric sleeve 70. In some embodiments, at least a portion of the second proximal section 96 of the second filament 94 is positioned within the second lateral recess 65 formed within the second leg 66 proximal of the second fabric sleeve 72. In at least some embodiments, the first filament 90 does not pass through the first leg 64 of the first locking portion or post member 60. In at least some embodiments, the second filament 94 does not pass through the second leg 66 of the first locking portion or post member 60. For example, the first leg 64 and/or the second leg 66 of the first locking portion or post member 60 may lack holes or apertures extending therethrough, thus reducing the processing and/or manufacturing time and cost of the first locking portion or post member 60.

In some embodiments, the first fabric sleeve 70 and/or the second fabric sleeve 72 may each be formed from a braided material. In some embodiments, the first fabric sleeve 70 and/or the second fabric sleeve 72 may each be formed from a polymeric material. In some embodiments, the first fabric sleeve 70 and/or the second fabric sleeve 72 may each be formed from a metallic material. In some embodiments, the first fabric sleeve 70 and/or the second fabric sleeve 72 may each be formed from other materials and/or combinations of materials providing sufficient flexibility, strength, and tear resistance. In some embodiments, at least the elastic central portion 702 of the first fabric sleeve 70 and/or the elastic central portion 722 of the second fabric sleeve 72 may be impregnated with an elastic polymeric material such as polyurethane or other suitable materials. In some embodiments, at least the elastic central portion 702 of the first fabric sleeve 70 and/or the elastic central portion 722 of the second fabric sleeve 72 may be formed from and/or include a collagen fabric configured to swell upon contact with fluid. In some embodiments, at least the elastic central portion 702 of the first fabric sleeve 70 and/or the elastic central portion 722 of the second fabric sleeve 72 may be formed from and/or include a braided material coated with and/or impregnated with a hydrogel configured to swell upon contact with fluid. Some examples of suitable but non-limiting materials for the first fabric sleeve 70, the second fabric sleeve 72, the first filament 90, the second filament 94, etc., for example metallic materials, polymeric materials, and/or braided materials are described below.

Figure 10:
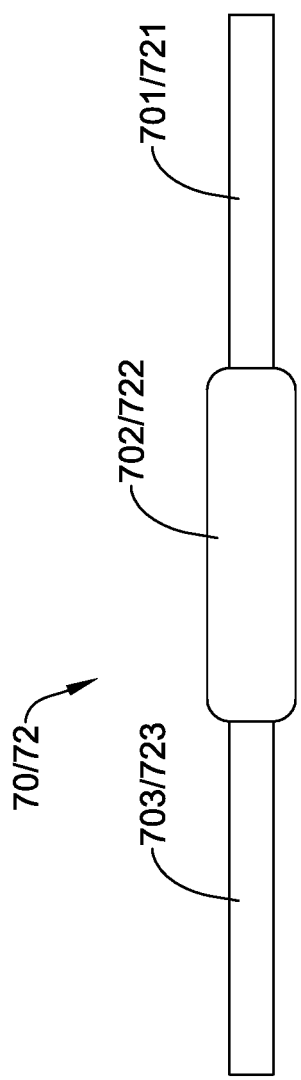
FIG. 10 is a top view of an example fabric sleeve in a relaxed state.
Figure 11:
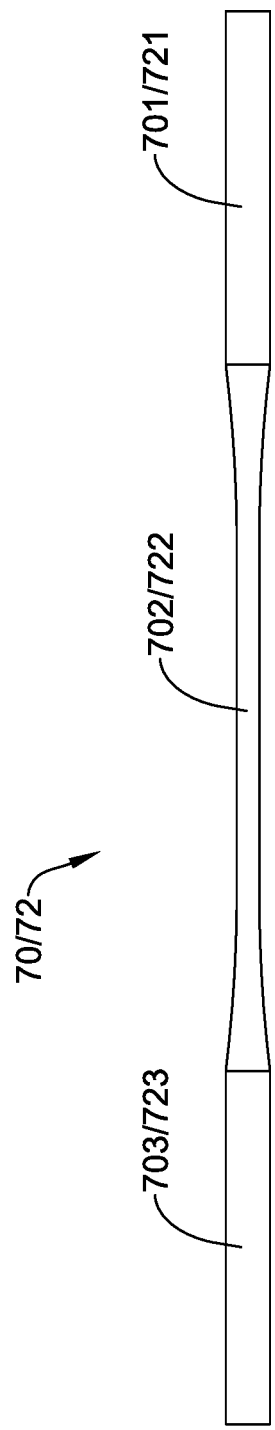
FIG. 11 is a top view of the example fabric sleeve of FIG. 10 in an elongated state.

The first fabric sleeve 70 and/or the second fabric sleeve 72 may be configured to shift between a relaxed state and an elongated state when the first fabric sleeve 70 and/or the second fabric sleeve 72 is placed in tension. FIGS. 10 and 11 illustrate the first fabric sleeve 70 and/or the second fabric sleeve 72 in the relaxed state and the elongated state, respectively. The relaxed state may be achieved and/or attained in the absence of a tensioning force applied to the first fabric sleeve 70 and/or the second fabric sleeve 72. For example, when tension applied to the first fabric sleeve 70 and/or the second fabric sleeve 72 is released, the first fabric sleeve 70 and/or the second fabric sleeve 72 may be biased and/or self-biased to return to, and/or may move or shift toward, the relaxed state. Each of the first end portion 701 of the first fabric sleeve 70, the second end portion 703 of the first fabric sleeve 70, and the elastic central portion 702 of the first fabric sleeve 70 may have a length and a thickness. Each of the first end portion 721 of the second fabric sleeve 72, the second end portion 723 of the second fabric sleeve 72, and the elastic central portion 722 of the second fabric sleeve 72 may have a length and a thickness.

Applying tension to and/or at the first end portion 701 of the first fabric sleeve 70 and the second end portion 703 of the first fabric sleeve 70 may cause the elastic central portion 702 of the first fabric sleeve 70 to stretch and/or elongate, as well as thin and/or reduce in thickness. Applying tension to and/or at the first end portion 721 of the second fabric sleeve 72 and the second end portion 723 of the second fabric sleeve 72 may cause the elastic central portion 722 of the second fabric sleeve 72 to stretch and/or elongate, as well as thin and/or reduce in thickness. For example, in some embodiments, the length of the elastic central portion 702 of the first fabric sleeve 70 and/or the length of the elastic central portion 722 of the second fabric sleeve 72 may be at least 50% greater in the elongated state than in the relaxed state. In some embodiments, the thickness of the elastic central portion 702 of the first fabric sleeve 70 and/or the thickness of the elastic central portion 722 of the second fabric sleeve 72 may be at least 50% less in the elongated state than in the relaxed state. For example, the thickness of the elastic central portion 702 of the first fabric sleeve 70 in the elongated state may be reduced compared to the thickness of elastic central portion 702 of the first fabric sleeve 70 in the relaxed state, and/or the thickness of the elastic central portion 722 of the second fabric sleeve 72 may be reduced compared to the thickness of the elastic central portion 722 of the second fabric sleeve 72 in the relaxed state.

In some embodiments, the first end portion 701 of the first fabric sleeve 70 and/or the second end portion 703 of the first fabric sleeve 70 may be configured to limit dimensional change under tension. In some embodiments, the length of the first end portion 701 of the first fabric sleeve 70 and/or the length of the second end portion 703 of the first fabric sleeve 70 may change less than 10% between the relaxed state and the elongated state. For example, the length of each of the first end portion 701 of the first fabric sleeve 70 and the second end portion 703 of the first fabric sleeve 70 may change less than 10% when the first fabric sleeve 70 is placed in tension. Similarly, the length of each of the first end portion 721 of the second fabric sleeve 72 and the second end portion 723 of the second fabric sleeve 72 may change less than 10% when the second fabric sleeve 72 is placed in tension. In some embodiments, the thickness of each of the first end portion 701 of the first fabric sleeve 70 and the second end portion 703 of the first fabric sleeve 70 may change less than 10% when the first fabric sleeve 70 is placed in tension. Similarly, the thickness of each of the first end portion 721 of the second fabric sleeve 72 and the second end portion 723 of the second fabric sleeve 72 may change less than 10% when the second fabric sleeve 72 is placed in tension.

Figure 12:
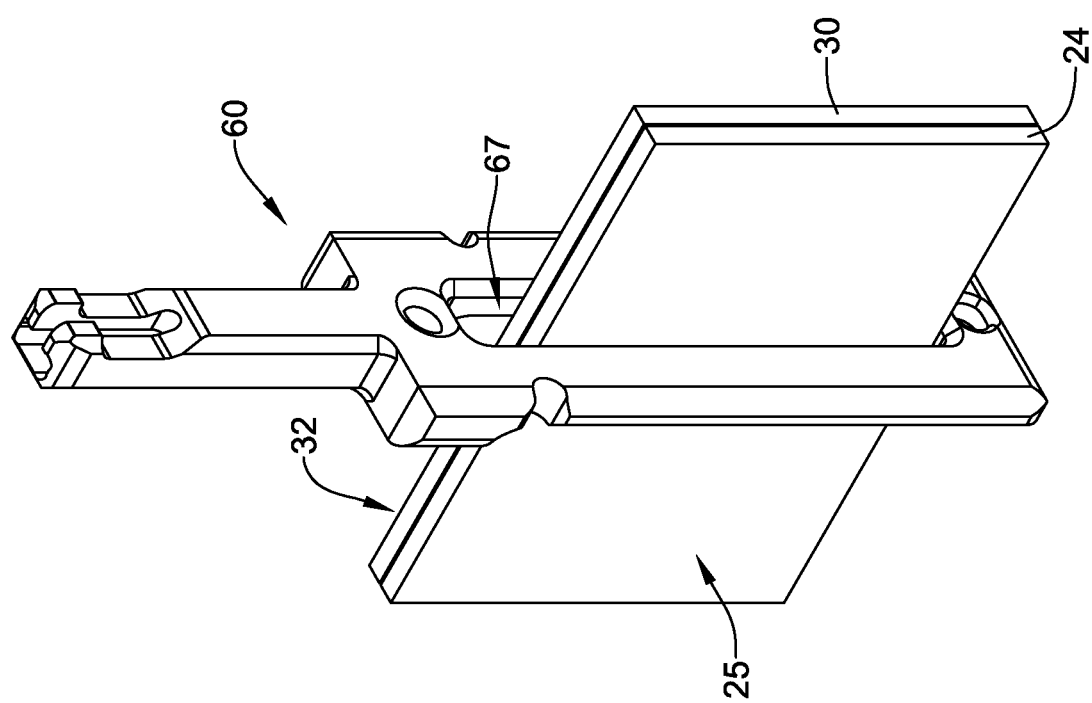
FIGS. 12-17 illustrate aspects of a method of assembling selected components of the replacement heart valve commissure assembly of FIG. 8.

FIGS. 12-17 illustrate selected elements in an example method of assembling of a replacement heart valve commissure assembly for use in the replacement heart valve implant 16. As shown in FIG. 12, the method may include inserting the first sleeve portion 25 of the first valve leaflet 24 and the second sleeve portion 32 of the second valve leaflet 30 through the longitudinally-oriented tissue slot 67 of the first locking portion or post member 60 of the locking mechanism 48, the locking mechanism 48 comprising the first locking portion or post member 60 and the second locking portion or buckle member 50.

Figure 13:
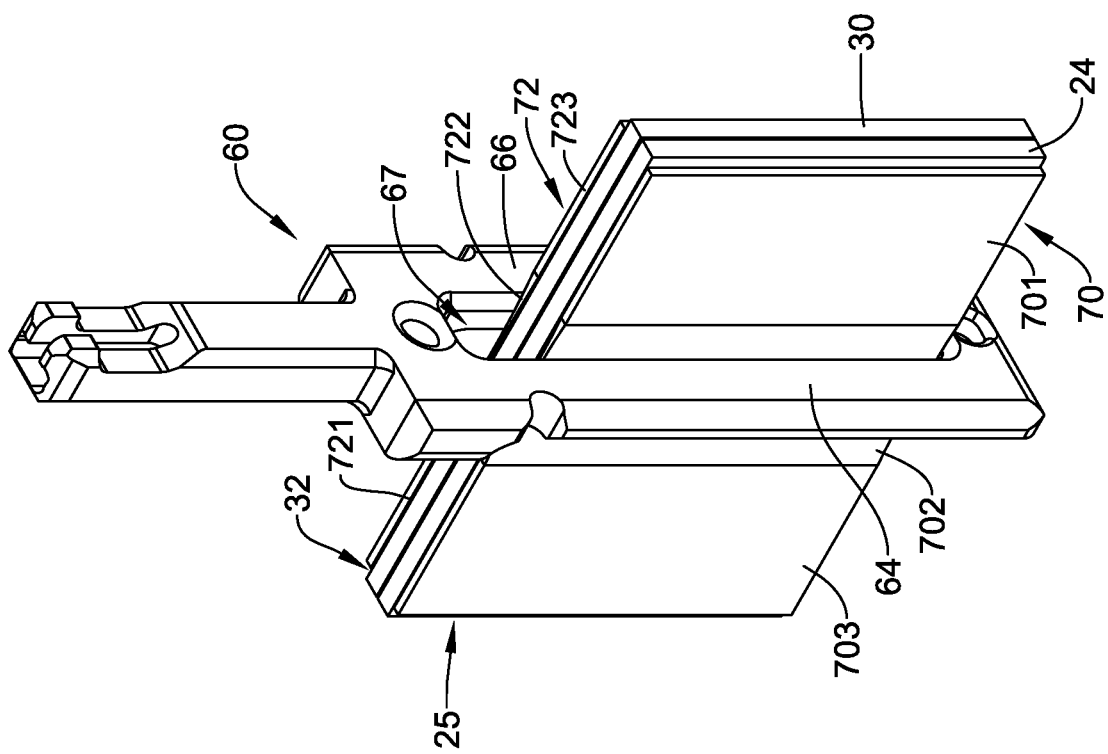

As seen in FIG. 13, the method may include inserting the first fabric sleeve 70 through the longitudinally-oriented tissue slot 67 under tension in the elongated state between the first sleeve portion 25 of the first valve leaflet 24 and the first leg 64 of the first locking portion or post member 60, and inserting the second fabric sleeve 72 through the longitudinally-oriented tissue slot 67 under tension in the elongated state between the second sleeve portion 32 of the second valve leaflet 30 and the second leg 66 of the first locking portion or post member 60. As noted above, the thickness of the elastic central portion 702 of the first fabric sleeve 70 in the elongated state is reduced compared to the thickness of the elastic central portion 702 of the first fabric sleeve 70 in the relaxed state, and the thickness of the elastic central portion 722 of the second fabric sleeve 72 in the elongated state is reduced compared to the thickness of the elastic central portion 722 of the second fabric sleeve 72 in the relaxed state.

The reduced thickness of the elastic central portion 702 of the first fabric sleeve 70 and/or the elastic central portion 722 of the second fabric sleeve 72 in the elongated state may facilitate positioning of the first fabric sleeve 70 and/or the second fabric sleeve 72 within the longitudinally-oriented tissue slot 67, because a width of the longitudinally-oriented tissue slot 67 (e.g., between the first leg 64 of the first locking portion or post member 60 and the second leg 66 of the first locking portion or post member 60) may be greater than a total thickness of the first sleeve portion 25 of the first valve leaflet 24, the second sleeve portion 32 of the second valve leaflet 30, the elastic central portion 702 of the first fabric sleeve 70 in the elongated state, and the elastic central portion 722 of the second fabric sleeve 72 in the elongated state. In addition or alternatively, in some embodiments, a width of the longitudinally-oriented tissue slot 67 (e.g., between the first leg 64 of the first locking portion or post member 60 and the second leg 66 of the first locking portion or post member 60) may be greater than a total thickness of the first sleeve portion 25 of the first valve leaflet 24, the second sleeve portion 32 of the second valve leaflet 30, the first end portion 701 or the second end portion 703 of the first fabric sleeve 70, and the first end portion 721 or the second end portion 723 of the second fabric sleeve 72.

In at least some embodiments, the thickness of the first valve leaflet 24 and/or the second valve leaflet 30 may be inconsistent and/or may vary slightly due to normal manufacturing variation, tolerance, etc. For example, the thickness of the material used to form the first valve leaflet 24 and/or the second valve leaflet 30 may vary by 5%, 10%, 15% or more. This variation may present challenges in fitment within the longitudinally-oriented tissue slot 67, which may have a substantially fixed width dimension. In some embodiments, a "loose" fit following assembly of the replacement heart valve commissure assembly may permit the leaflets to move around within the longitudinally-oriented tissue slot 67, which may result in increased stress, friction, and/or wear on the leaflet material.

Accordingly, the first fabric sleeve 70 and/or the second fabric sleeve 72 may be configured such that the thickness of the elastic central portion 702 of the first fabric sleeve 70 in the relaxed state increases compared to the thickness of the elastic central portion 702 of the first fabric sleeve 70 in the elongated state, and the thickness of the elastic central portion 722 of the second fabric sleeve 72 in the relaxed state increases compared to the thickness of the elastic central portion 722 of the second fabric sleeve 72 in the elongated state. For example, the elastic central portion 702 of the first fabric sleeve 70 and/or the elastic central portion 722 of the second fabric sleeve 72 may be configured to exert a compressive force on and/or against the first leg 64 of the first locking portion or post member 60 and the second leg 66 of the first locking portion or post member 60 when the tension is released (e.g., when the elastic central portion 702 of the first fabric sleeve 70 and/or the elastic central portion 722 of the second fabric sleeve 72 shifts toward the relaxed state).

In some embodiments, the method may further include aligning a profile (e.g., an outer perimeter, an outer edge, etc.) of the first sleeve portion 25 of the first valve leaflet 24 with a profile of the first fabric sleeve 70 and/or a profile of the first overlapped portion 71 of the first fabric sleeve 70, and aligning a profile of the second sleeve portion 32 of the second valve leaflet 30 with a profile of the second fabric sleeve 72 and/or a profile of the second overlapped portion 73 of the second fabric sleeve 72.

Figure 14:
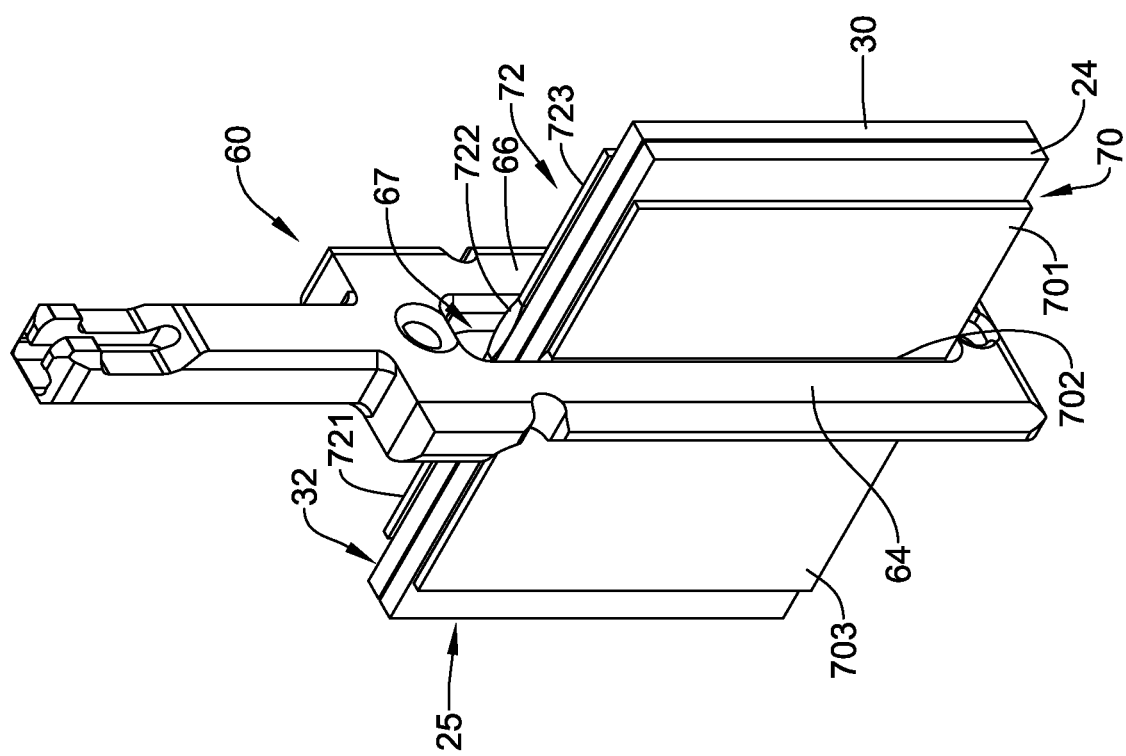

FIG. 14 illustrates a step in the method of releasing the tension on the first fabric sleeve 70 and the second fabric sleeve 72 such that the elastic central portion 702 of the first fabric sleeve 70 and the elastic central portion 722 of the second fabric sleeve 72 shifts toward the relaxed state and increases in thickness to place the first sleeve portion 25 of the first valve leaflet 24 and the second sleeve portion 32 of the second valve leaflet 30 in compression between the first leg 64 of the first locking portion or post member 60 and the second leg 66 of the first locking portion or post member 60. Expansion of the elastic central portion 702 of the first fabric sleeve 70 and/or the elastic central portion 722 of the second fabric sleeve 72 allows for and/or manages the variable thickness of the valve leaflets by taking up any empty space between the first leg 64 of the first locking portion or post member 60 and the second leg 66 of the first locking portion or post member 60 to create a compressive interference fit between the valve leaflets and the legs of the first locking portion or post member 60. In at least some examples, the elastic central portion 702 of the first fabric sleeve 70 and/or the elastic central portion 722 of the second fabric sleeve 72 does not fully return to the relaxed state when the tension is released but remains biased toward the relaxed state.

Figure 15:
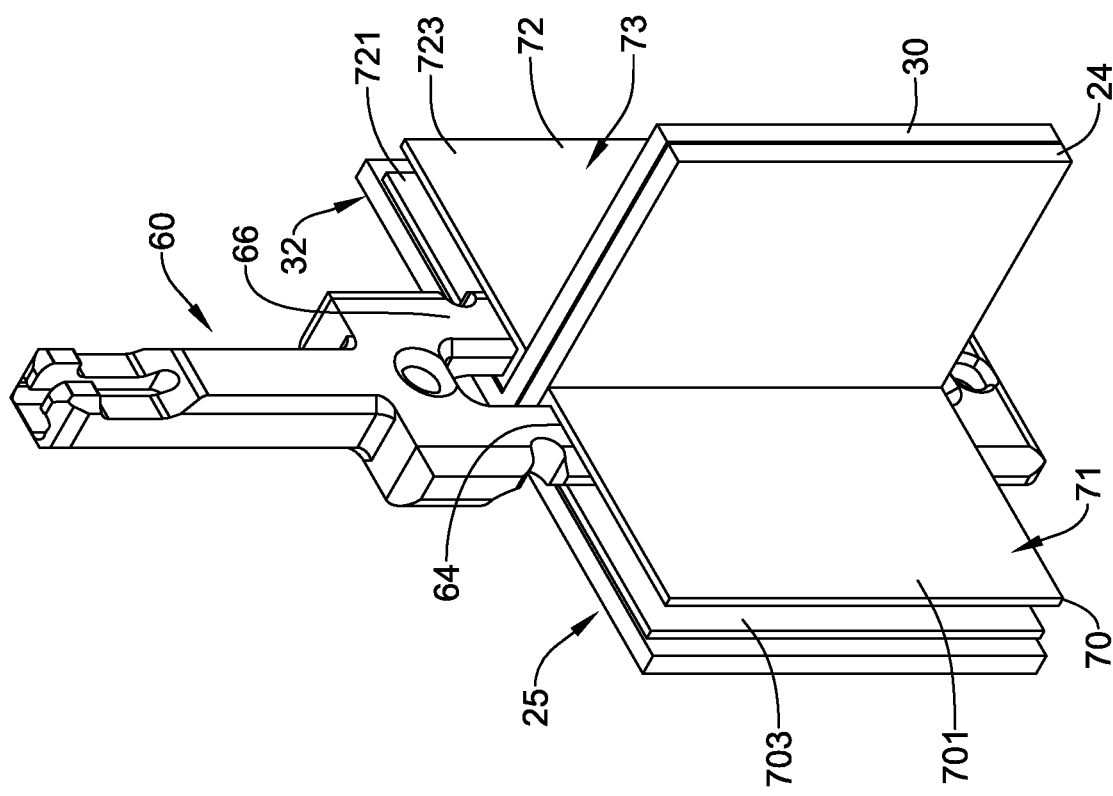

As seen in FIG. 15, the method may include wrapping the first fabric sleeve 70 around the first leg 64 of the first locking portion or post member 60 such that the first fabric sleeve 70 overlaps itself adjacent the first sleeve portion 25 of the first valve leaflet 24 to form a first overlapped portion 71 of the first fabric sleeve 70, and wrapping the second fabric sleeve 72 around the second leg 66 of the first locking portion or post member 60 such that the second fabric sleeve 72 overlaps itself adjacent the second sleeve portion 32 of the second valve leaflet 30 to form a second overlapped portion 73 of the second fabric sleeve 72.

Figure 16:
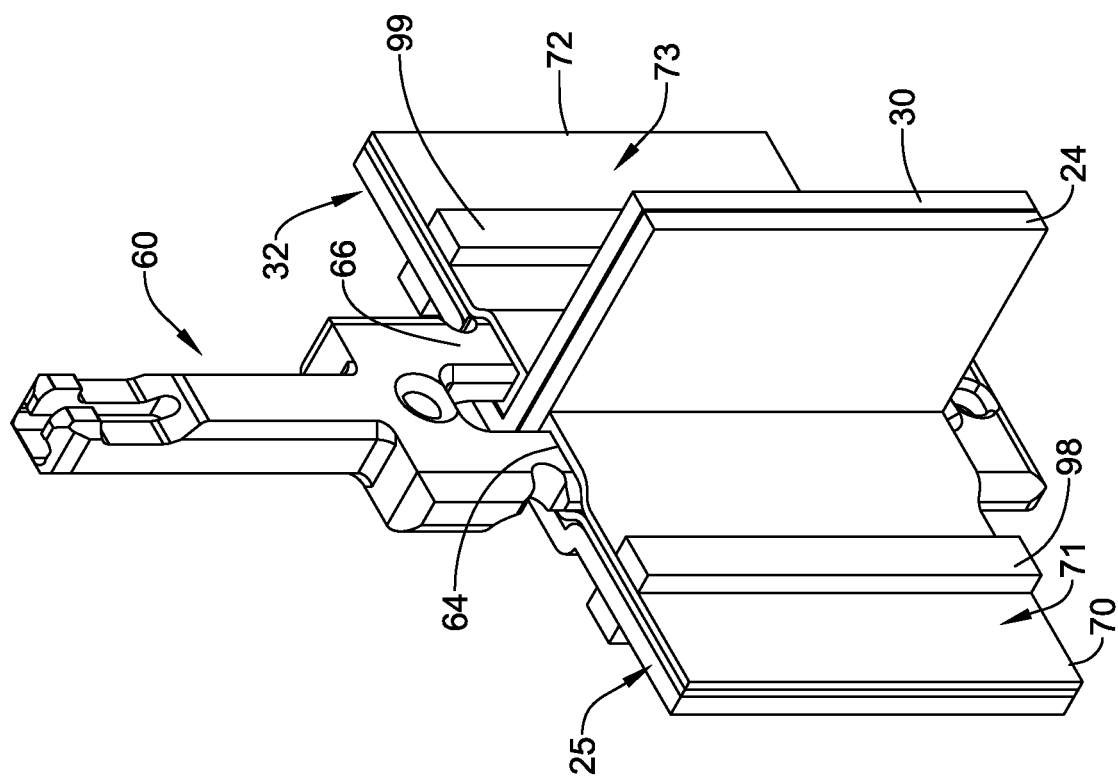

As seen in FIG. 16, the method may include clamping the first overlapped portion 71 of the first fabric sleeve 70 to the first sleeve portion 25 of the first valve leaflet 24 using a first clamping element 98, and clamping the second overlapped portion 73 of the second fabric sleeve 72 to the second sleeve portion 32 of the second valve leaflet 30 using a second clamping element 99. In some embodiments, the first clamping element 98 and the second clamping element 99 may be independent and/or separate structures. In some embodiments, the first clamping element 98 and the second clamping element 99 may be joined together, may be joined to a common fixture, and/or may be a single structure. Other configurations are also contemplated.

Figure 17:
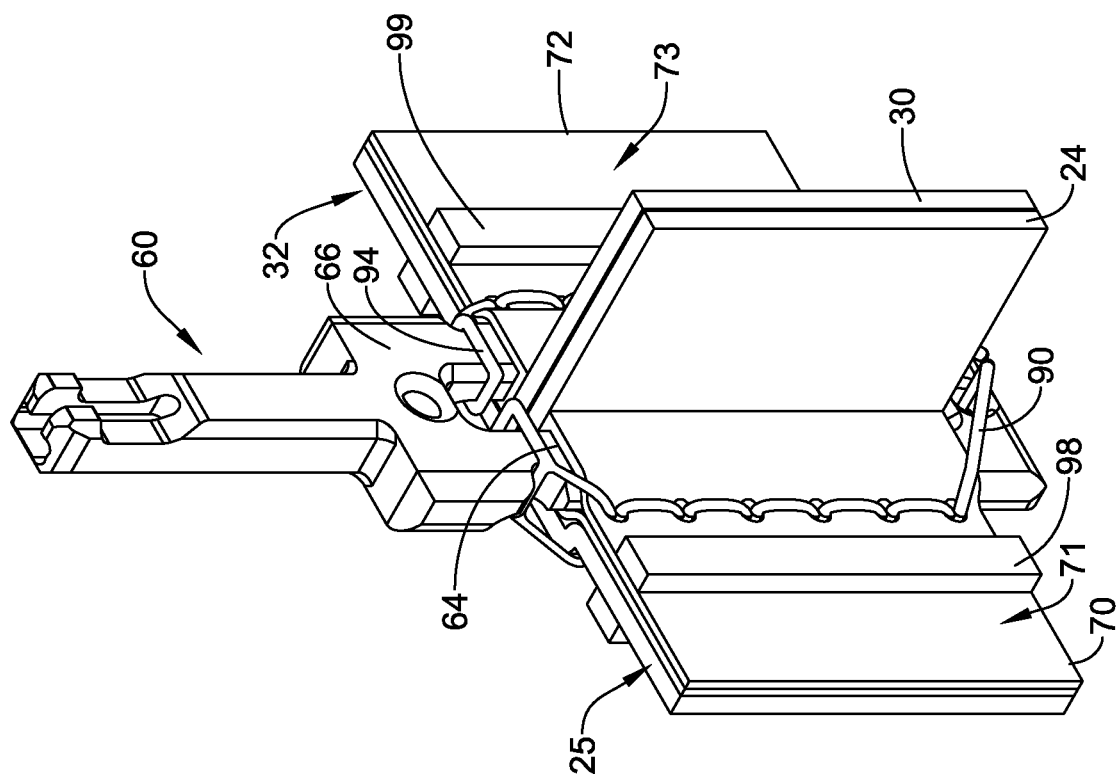

As shown in FIG. 17, the method may include fixedly attaching the first overlapped portion 71 of the first fabric sleeve 70 to the first sleeve portion 25 of the first valve leaflet 24 using the first filament 90, as described above, and fixedly attaching the second overlapped portion 73 of the second fabric sleeve 72 to the second sleeve portion 32 of the second valve leaflet 30 using the second filament 94, as described above. In some embodiments, the first overlapped portion 71 of the first fabric sleeve 70 is fixedly attached to the first sleeve portion 25 of the first valve leaflet 24 using a linear joining pattern and/or linearly-aligned stitches of the first filament 90, and the second overlapped portion 73 of the second fabric sleeve 72 is fixedly attached to the second sleeve portion 32 of the second valve leaflet 30 using a linear joining pattern and/or linearly-aligned stitches of the second filament 94.

Figure 18:
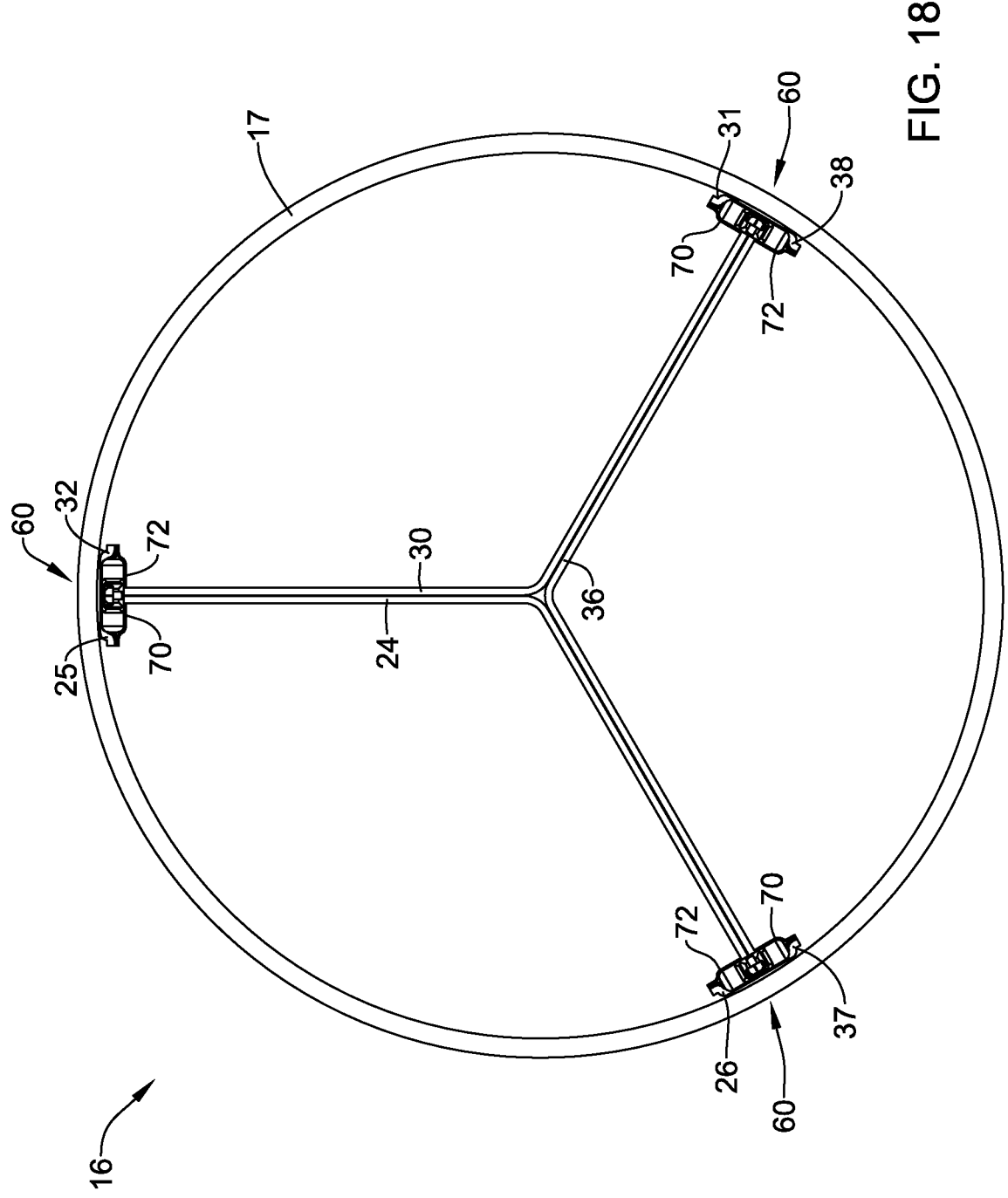
FIG. 18 is a top view of selected components of the example replacement heart valve implant of FIG. 2.

As mentioned above, there may be multiple instances of certain singularly-described features present in the disclosed device(s) and/or apparatus. Merely as an example to improve understanding of certain features, FIG. 18 illustrates a top view of selected elements of the replacement heart valve implant 16. As may be seen in FIG. 18, the replacement heart valve implant 16 may include an expandable anchor member 17, a first locking mechanism including a first locking portion or post member 60, a second locking mechanism including a first locking portion or post member 60, and a third locking mechanism including a first locking portion or post member 60. Each locking mechanism and/or first locking portion or post member 60 may be identical to the others, or there may be differences between them depending upon the requirements of the replacement heart valve implant 16. The replacement heart valve implant 16 may include a first valve leaflet 24 having a first sleeve portion 25 and an opposing second sleeve portion 26, a second valve leaflet 30 having a first sleeve portion 31 and an opposing second sleeve portion 32, and a third valve leaflet 36 having a first sleeve portion 37 and an opposing second sleeve portion 38.

The first sleeve portion 25 of the first valve leaflet 24 and the second sleeve portion 32 of the second valve leaflet 30 may pass though the longitudinally-oriented tissue slot of the first locking portion or post member 60 of the first locking mechanism, as described above. The first sleeve portion 31 of the second valve leaflet 30 and the second sleeve portion 38 of the third valve leaflet 36 may pass though the longitudinally-oriented tissue slot of the first locking portion or post member 60 of the second locking mechanism. The first sleeve portion 37 of the third valve leaflet 36 and the second sleeve portion 26 of the first valve leaflet 24 may pass though the longitudinally-oriented tissue slot of the first locking portion or post member 60 of the third locking mechanism.

The materials that can be used for the various components of the medical device system 10, the outer sheath 12, the inner sheath or catheter 14, the replacement heart valve implant 16, the handle 18, etc. (and/or other systems disclosed herein) and the various elements thereof disclosed herein may include those commonly associated with medical devices. For simplicity purposes, the following discussion makes reference to the medical device system 10, the outer sheath 12, the inner sheath or catheter 14, the replacement heart valve implant 16, the handle 18, etc. However, this is not intended to limit the devices and methods described herein, as the discussion may be applied to other elements, members, components, or devices disclosed herein, such as, but not limited to, the actuator element(s) 15, the seal member 20, the plurality of valve leaflets 22, the expandable anchor member 17, the second locking portion or buckle members 50, the first locking portion or post member 60, the first fabric sleeve 70, the second fabric sleeve 72, the collars 80, the guides 82, the first filament 90, the second filament 94, etc., and/or elements or components thereof.

In some embodiments, the medical device system 10, the outer sheath 12, the inner sheath or catheter 14, the replacement heart valve implant 16, the handle 18, etc., and/or components thereof (such as, but not limited to, the actuator element(s) 15, the seal member 20, the plurality of valve leaflets 22, the expandable anchor member 17, the second locking portion or buckle members 50, the first locking portion or post member 60, the first fabric sleeve 70, the second fabric sleeve 72, the collars 80, the guides 82, the first filament 90, the second filament 94, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the medical device system 10, the outer sheath 12, the inner sheath or catheter 14, the replacement heart valve implant 16, the handle 18, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the medical device system 10, the outer sheath 12, the inner sheath or catheter 14, the replacement heart valve implant 16, the handle 18, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10, the outer sheath 12, the inner sheath or catheter 14, the replacement heart valve implant 16, the handle 18, etc. to achieve the same result.

In some embodiments, a degree of Magnetic Resonance Imaging (Mill) compatibility is imparted into the medical device system 10, the outer sheath 12, the inner sheath or catheter 14, the replacement heart valve implant 16, the handle 18, etc. For example, the medical device system 10, the outer sheath 12, the inner sheath or catheter 14, the replacement heart valve implant 16, the handle 18, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The medical device system 10, the outer sheath 12, the inner sheath or catheter 14, the replacement heart valve implant 16, the handle 18, etc., or portions thereof, may also be made from a material that the Mill machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the medical device system 10, the outer sheath 12, the inner sheath or catheter 14, the replacement heart valve implant 16, the handle 18, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the medical device system 10, the outer sheath 12, the inner sheath or catheter 14, the replacement heart valve implant 16, the handle 18, the first fabric sleeve 70, the second fabric sleeve 72, etc. and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the medical device system 10, the outer sheath 12, the inner sheath or catheter 14, the replacement heart valve implant 16, the handle 18, the first fabric sleeve 70, the second fabric sleeve 72, the first filament 90, the second filament 94, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the medical device system 10, the outer sheath 12, the inner sheath or catheter 14, the replacement heart valve implant 16, the handle 18, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made to details, particularly in matters of shape, size, and arrangement of steps, without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A replacement heart valve commissure assembly, comprising:
    at least one commissure post having an elongated proximal portion, a first leg fixedly attached to and extending distally from the elongated proximal portion, and a second leg fixedly attached to and extending distally from the elongated proximal portion,
    wherein the first leg and the second leg define a longitudinally-oriented tissue slot extending through the at least one commissure post in a radial direction relative to a central longitudinal axis of a replacement heart valve;
    a first valve leaflet passing through the longitudinally-oriented tissue slot in a radially outward direction and secured to a first fabric sleeve that receives the first leg;
    a second valve leaflet passing through the longitudinally-oriented tissue slot in a radially outward direction and secured to a second fabric sleeve that receives the second leg;
    wherein a first sleeve portion of the first valve leaflet is fixedly attached to the first fabric sleeve and a second sleeve portion of the second valve leaflet is fixedly attached to the second fabric sleeve;
    wherein the first fabric sleeve includes an elastic central portion configured to receive the first leg,
    wherein the second fabric sleeve includes an elastic central portion configured to receive the second leg, and each elastic central portion has a length and a thickness in a relaxed state,
    wherein a width of the longitudinally-oriented tissue slot is less than a total thickness of the first sleeve portion of the first valve leaflet, the second sleeve portion of the second valve leaflet, the elastic central portion of the first fabric sleeve in a relaxed state, and an elastic central portion of the second fabric sleeve in a relaxed state.

2. The replacement heart valve commissure assembly of claim 1, wherein the first fabric sleeve is configured to shift between the relaxed state and an elongated state when the first fabric sleeve is placed in tension.

3. The replacement heart valve commissure assembly of claim 2, wherein the elastic central portion of the first fabric sleeve is configured to exert a compressive force on the first leg when the tension is released.

4. The replacement heart valve commissure assembly of claim 2, wherein the length of the elastic central portion of the first fabric sleeve is at least 50% greater in the elongated state than in the relaxed state.

5. The replacement heart valve commissure assembly of claim 2, wherein the thickness of the elastic central portion of the first fabric sleeve is at least 50% less in the elongated state than in the relaxed state.

6. The replacement heart valve commissure assembly of claim 2, wherein
    the first sleeve portion of the first valve leaflet and the second sleeve portion of the second valve leaflet both pass through the longitudinally-oriented tissue slot.

7. The replacement heart valve commissure assembly of claim 6, wherein a width of the longitudinally-oriented tissue slot is greater than a total thickness of the first sleeve portion of the first valve leaflet, the second sleeve portion of the second valve leaflet, the elastic central portion of the first fabric sleeve in the elongated state, and an elastic central portion of the second fabric sleeve in the elongated state.

8. The replacement heart valve commissure assembly of claim 1, wherein the first sleeve portion of the first valve leaflet is fixedly attached to the first fabric sleeve with one or more stitches of a first filament oriented generally parallel to the first leg of the at least one commissure post.

9. The replacement heart valve commissure assembly of claim 1, wherein the second sleeve portion of the second valve leaflet is fixedly attached to the second fabric sleeve with one or more stitches of a second filament oriented generally parallel to the second leg of the at least one commissure post.

10. A replacement heart valve implant, comprising:
    an expandable anchor member actuatable between a delivery configuration and a deployed configuration;
    a replacement heart valve commissure assembly, comprising:
    at least one commissure post having an elongated proximal portion, a first leg fixedly attached to and extending distally from the elongated proximal portion, and a second leg fixedly attached to and extending distally from the elongated proximal portion,
    wherein the first leg and the second leg define a longitudinally-oriented slot extending through the at least one commissure post in a radial direction relative to a central longitudinal axis of a replacement heart valve;
    a first valve leaflet passing through the longitudinally-oriented slot in a radially outward direction and secured to the first leg; and
    a second valve leaflet passing through the longitudinally-oriented slot in a radially outward direction and secured to the second leg;
    wherein a first sleeve portion of the first valve leaflet is fixedly attached to a first fabric sleeve wrapped around a first leg of the at least one commissure post, and a second sleeve portion of the second valve leaflet is fixedly attached to a second fabric sleeve wrapped around a second leg of the at least one commissure post;
    wherein the first fabric sleeve is configured to receive the first leg and has a first length and a first thickness in a relaxed state and has a greater second length and a lesser second thickness when under longitudinal tension;
    wherein the second fabric sleeve is configured to receive the first leg and has a first length and a first thickness in a relaxed state and has a greater second length and a lesser second thickness when under longitudinal tension,
    wherein a width of the longitudinally-oriented tissue slot is less than a total thickness of the first sleeve portion of the first valve leaflet, the second sleeve portion of the second valve leaflet, the elastic central portion of the first fabric sleeve in a relaxed state, and an elastic central portion of the second fabric sleeve in a relaxed state.

11. The replacement heart valve implant of claim 10, further comprising a polymeric seal member disposed on an outer surface of the expandable anchor member and attached to a distal end of the expandable anchor member.

12. The replacement heart valve implant of claim 10, wherein the first fabric sleeve and the second fabric sleeve are each formed from a braided material.

13. The replacement heart valve implant of claim 10, wherein at least the elastic central portion of each of the first fabric sleeve and the second fabric sleeve is impregnated with polyurethane.

* * * * *